US009808281B2

(12) United States Patent
Solitario, Jr. et al.

(10) Patent No.: US 9,808,281 B2
(45) Date of Patent: Nov. 7, 2017

(54) PATIENT-MOUNTED RETRACTION

(75) Inventors: Ralph C. Solitario, Jr., West Chester, PA (US); Brian Bankoski, West Grove, PA (US); Mark Rossney, West Chester, PA (US); Santiago Figuereo, Miami Beach, FL (US); Robert Bohinski, Cincinnati, OH (US)

(73) Assignee: DePuy Synthes Products, Inc., Raynham, MA (US)

( * ) Notice: Subject to any disclaimer, the term of this patent is extended or adjusted under 35 U.S.C. 154(b) by 311 days.

(21) Appl. No.: 12/784,051

(22) Filed: May 20, 2010

(65) Prior Publication Data
US 2011/0130634 A1 Jun. 2, 2011

Related U.S. Application Data

(60) Provisional application No. 61/179,924, filed on May 20, 2009.

(51) Int. Cl.
*A61B 17/70* (2006.01)
*A61B 17/34* (2006.01)
*A61B 17/02* (2006.01)

(52) U.S. Cl.
CPC ...... *A61B 17/3421* (2013.01); *A61B 17/3439* (2013.01); *A61B 17/7035* (2013.01);
(Continued)

(58) Field of Classification Search
CPC ....... A61B 1/313; A61B 1/3135; A61B 1/317; A61B 17/7085; A61B 2017/0256; A61B 17/7083; A61B 17/0218; A61B 17/0206; A61B 17/025; A61B 1/32; A61B 17/708; A61B 17/7077
(Continued)

(56) References Cited

U.S. PATENT DOCUMENTS 2,250,417 A 7/1941 Ettinger
2,373,478 A 4/1945 Kuhn
(Continued)

FOREIGN PATENT DOCUMENTS

AU A-13672-95 9/1995
AU 06977/05 B2 10/1998
(Continued)

OTHER PUBLICATIONS

"Xia Spinal System", Stryker Howmedica Osteonics, 1999, 8 pages.
(Continued)

*Primary Examiner* — Lynnsy Summitt
(74) *Attorney, Agent, or Firm* — Baker & Hostetler LLP

(57) ABSTRACT

Patient-mounted retractors with varying configurations and/or features are provided, along with additional components for use therewith in provided patient-mounted retractor assemblies. Blade type and tube type patient-mounted retractors that may be re-positioned during the course of a procedure are provided in varying configurations and/or geometries suitable for varying procedures and/or patient anatomies. Applications of re-positionable patient-mounted retractor assemblies are particularly suitable for use in minimally invasive procedures, eliminating the need for table-mounted retraction assemblies and/or cannulas that restrict the operating environment.

47 Claims, 14 Drawing Sheets

(52) U.S. Cl.
CPC .............. *A61B 2017/0256* (2013.01); *A61B 2017/3419* (2013.01)

(58) Field of Classification Search
USPC .......... 600/201–246; 606/99, 104, 86 A, 90, 606/246, 247, 250–279, 300, 301, 302, 606/304–308, 320, 322, 323
See application file for complete search history.

(56) References Cited

U.S. PATENT DOCUMENTS

| | | |
|---|---|---|
| 3,575,405 A | 4/1971 | Harding |
| 3,604,487 A | 9/1971 | Gilbert et al. |
| 4,335,715 A | 6/1982 | Kirkley |
| 4,409,968 A | 10/1983 | Drummond |
| 4,411,259 A | 10/1983 | Drummond |
| 4,545,374 A | 10/1985 | Jacobson |
| 4,733,657 A | 3/1988 | Kluger |
| 4,817,587 A | 4/1989 | Janese |
| 4,827,918 A | 5/1989 | Olerud |
| 4,904,010 A | 2/1990 | Lacey et al. |
| 4,957,495 A | 9/1990 | Kluger |
| 5,015,247 A | 5/1991 | Michelson |
| 5,020,519 A | 6/1991 | Hayes et al. |
| 5,047,029 A | 9/1991 | Aebi |
| D331,625 S | 12/1992 | Price et al. |
| 5,171,279 A | 12/1992 | Mathews |
| 5,207,678 A | 5/1993 | Harms et al. |
| 5,217,497 A | 6/1993 | Mehdian |
| 5,219,349 A | 6/1993 | Krag et al. |
| 5,242,443 A | 9/1993 | Kambin |
| 5,312,404 A | 5/1994 | Asher et al. |
| 5,344,422 A | 9/1994 | Frigg |
| 5,352,231 A | 10/1994 | Brumfield et al. |
| 5,360,431 A | 11/1994 | Puno et al. |
| 5,431,658 A | 7/1995 | Moskovich |
| 5,433,467 A | 7/1995 | Easterwood |
| 5,439,464 A | 8/1995 | Shapiro |
| 5,443,467 A | 8/1995 | Biedermann et al. |
| 5,474,555 A | 12/1995 | Puno et al. |
| 5,484,440 A | 1/1996 | Allard |
| 5,487,744 A | 1/1996 | Howland |
| 5,498,262 A | 3/1996 | Bryan |
| 5,501,684 A | 3/1996 | Schlapfer et al. |
| 5,507,211 A | 4/1996 | Wagner |
| 5,520,690 A | 5/1996 | Errico et al. |
| 5,529,571 A | 6/1996 | Daniel |
| 5,531,746 A | 7/1996 | Errico et al. |
| 5,547,873 A | 8/1996 | Magneson et al. |
| 5,562,661 A | 10/1996 | Yoshimi et al. |
| 5,605,458 A | 2/1997 | Bailey et al. |
| 5,607,426 A | 3/1997 | Ralph et al. |
| 5,611,800 A | 3/1997 | Davis et al. |
| 5,613,968 A | 3/1997 | Lin |
| 5,624,441 A | 4/1997 | Sherman et al. |
| 5,624,442 A | 4/1997 | Mellinger et al. |
| 5,647,873 A | 7/1997 | Errico et al. |
| 5,649,931 A | 7/1997 | Bryant et al. |
| 5,667,506 A | 9/1997 | Sutterlin |
| 5,667,513 A | 9/1997 | Torrie et al. |
| 5,669,911 A | 9/1997 | Errico et al. |
| 5,676,664 A | 10/1997 | Allard et al. |
| 5,690,630 A | 11/1997 | Errico et al. |
| 5,707,371 A | 1/1998 | Metz-Stavenhagen |
| 5,720,751 A | 2/1998 | Jackson |
| 5,725,588 A | 3/1998 | Errico et al. |
| 5,728,046 A | 3/1998 | Mayer |
| 5,732,992 A | 3/1998 | Mauldin |
| 5,782,830 A | 7/1998 | Farris |
| 5,782,833 A | 7/1998 | Haider |
| 5,797,911 A | 8/1998 | Sherman et al. |
| 5,810,878 A | 9/1998 | Burel et al. |
| 5,817,094 A | 10/1998 | Errico et al. |
| 5,863,293 A | 1/1999 | Richelsoph |
| 5,876,402 A | 3/1999 | Errico et al. |
| 5,879,350 A | 3/1999 | Sherman et al. |
| 5,882,350 A | 3/1999 | Ralph et al. |
| 5,885,285 A | 3/1999 | Simonson |
| 5,885,286 A | 3/1999 | Sherman et al. |
| 5,888,204 A | 3/1999 | Ralph et al. |
| 5,910,141 A | 6/1999 | Morrison et al. |
| 5,928,139 A | 7/1999 | Koros et al. |
| 5,938,663 A | 8/1999 | Petreto |
| 5,946,988 A | 9/1999 | Metz-Stavenhagen |
| 5,951,559 A | 9/1999 | Burkhart |
| 5,964,760 A | 10/1999 | Richelsoph |
| 5,964,761 A | 10/1999 | Kambin |
| 5,991,997 A | 11/1999 | Schley et al. |
| 6,010,503 A | 1/2000 | Richelsoph et al. |
| 6,022,350 A | 2/2000 | Ganem |
| 6,030,388 A | 2/2000 | Yoshimi et al. |
| 6,053,917 A | 4/2000 | Sherman et al. |
| 6,055,456 A | 4/2000 | Gerber |
| 6,066,174 A | 5/2000 | Farris |
| 6,074,391 A | 6/2000 | Metz-Stavenhagen et al. |
| 6,077,262 A | 6/2000 | Schlapfer et al. |
| 6,090,110 A | 7/2000 | Metz-Stavenhagen |
| 6,090,111 A | 7/2000 | Nichols |
| 6,090,113 A | 7/2000 | Le Couedic et al. |
| 6,132,432 A | 10/2000 | Richelsoph |
| 6,139,493 A | 10/2000 | Koros et al. |
| 6,139,549 A | 10/2000 | Keller |
| 6,146,383 A | 11/2000 | Studer et al. |
| 6,149,653 A | 11/2000 | Deslauriers |
| 6,159,214 A | 12/2000 | Michelson |
| 6,179,838 B1 | 1/2001 | Fiz |
| 6,183,472 B1 | 2/2001 | Lutz |
| 6,187,005 B1 | 2/2001 | Brace et al. |
| 6,189,422 B1 | 2/2001 | Stihl |
| 6,200,322 B1 | 3/2001 | Branch et al. |
| 6,206,826 B1 | 3/2001 | Mathews et al. |
| 6,214,006 B1 | 4/2001 | Metz-Stavenhagen |
| 6,224,598 B1 | 5/2001 | Jackson |
| 6,224,603 B1 | 5/2001 | Marino |
| 6,235,028 B1 | 5/2001 | Brumfield et al. |
| 6,251,112 B1 | 6/2001 | Jackson |
| 6,261,287 B1 | 7/2001 | Metz-Stavenhagen |
| 6,280,442 B1 | 8/2001 | Barker et al. |
| 6,302,410 B1 | 10/2001 | Wentworth et al. |
| 6,302,888 B1 | 10/2001 | Mellinger et al. |
| 6,355,040 B1 | 3/2002 | Richelsoph et al. |
| 6,360,750 B1 | 3/2002 | Gerber et al. |
| 6,361,535 B2 | 3/2002 | Jackson |
| RE37,665 E | 4/2002 | Ralph et al. |
| 6,368,321 B1 | 4/2002 | Jackson |
| 6,402,749 B1 | 6/2002 | Ashman |
| 6,415,693 B1 | 7/2002 | Simon et al. |
| 6,440,113 B1 | 8/2002 | Brisebois et al. |
| 6,440,133 B1 | 8/2002 | Beale et al. |
| 6,475,218 B2 | 11/2002 | Gournay et al. |
| 6,485,491 B1 | 11/2002 | Farris et al. |
| 6,488,681 B2 | 12/2002 | Martin et al. |
| 6,488,682 B2 | 12/2002 | Kikuchi et al. |
| 6,512,958 B1 | 1/2003 | Swoyer et al. |
| 6,520,907 B1 | 2/2003 | Foley et al. |
| 6,530,926 B1 | 3/2003 | Davison |
| 6,530,929 B1 | 3/2003 | Justis et al. |
| 6,537,276 B2 | 3/2003 | Metz-Stavenhagen |
| 6,543,317 B1 | 4/2003 | Rinner et al. |
| 6,554,834 B1 | 4/2003 | Crozet et al. |
| 6,558,387 B2 | 5/2003 | Errico et al. |
| 6,565,565 B1 | 5/2003 | Yuan et al. |
| 6,579,291 B1 | 6/2003 | Keith et al. |
| 6,579,292 B2 | 6/2003 | Taylor |
| 6,610,065 B1 | 8/2003 | Branch et al. |
| 6,613,091 B1 | 9/2003 | Zdeblick et al. |
| 6,623,485 B2 | 9/2003 | Doubler et al. |
| 6,626,347 B2 | 9/2003 | Ng |
| 6,626,905 B1 | 9/2003 | Schmiel et al. |
| 6,626,906 B1 | 9/2003 | Young |
| 6,648,888 B1 | 11/2003 | Shluzas |
| 6,660,004 B2 | 12/2003 | Barker et al. |
| 6,669,729 B2 | 12/2003 | Chin |
| 6,673,074 B2 | 1/2004 | Shluzas |

(56) References Cited

U.S. PATENT DOCUMENTS

| | | | |
|---|---|---|---|
| 6,676,661 B1 | 1/2004 | Martin et al. | |
| 6,716,214 B1 | 4/2004 | Jackson | |
| 6,719,758 B2 | 4/2004 | Beger et al. | |
| 6,726,692 B2 | 4/2004 | Bette | |
| 6,736,816 B2 | 5/2004 | Ritland | |
| 6,743,231 B1 | 6/2004 | Gray et al. | |
| 6,755,830 B2 | 6/2004 | Minfelde et al. | |
| 6,780,186 B2 | 8/2004 | Errico et al. | |
| 6,783,527 B2 | 8/2004 | Drewry et al. | |
| 6,790,208 B2 | 9/2004 | Oribe et al. | |
| 6,800,084 B2 | 10/2004 | Davison et al. | |
| 6,821,277 B2 | 11/2004 | Teitelbaum | |
| 6,827,722 B1 | 12/2004 | Schoenefeld | |
| 6,835,196 B2 | 12/2004 | Biedermann et al. | |
| 6,843,791 B2 | 1/2005 | Serhan | |
| 6,849,064 B2 | 2/2005 | Hamada | |
| 6,866,664 B2 | 3/2005 | Schär et al. | |
| 6,872,209 B2 | 3/2005 | Morrison | |
| 6,929,606 B2 | 8/2005 | Ritland | |
| 6,945,933 B2 | 9/2005 | Branch et al. | |
| 7,008,422 B2 | 3/2006 | Foley et al. | |
| 7,011,658 B2 | 3/2006 | Young | |
| 7,011,660 B2 | 3/2006 | Sherman et al. | |
| 7,018,379 B2 | 3/2006 | Drewry et al. | |
| RE39,089 E | 5/2006 | Ralph et al. | |
| 7,066,939 B2 | 6/2006 | Taylor | |
| 7,083,621 B2 | 8/2006 | Shaolian et al. | |
| 7,094,237 B2 | 8/2006 | Gradel et al. | |
| 7,104,992 B2 | 9/2006 | Bailey | |
| 7,128,743 B2 | 10/2006 | Metz-Stavenhagen | |
| 7,160,300 B2 | 1/2007 | Jackson | |
| 7,166,109 B2 | 1/2007 | Biedermann et al. | |
| 7,179,225 B2 | 2/2007 | Shluzas et al. | |
| 7,179,261 B2 | 2/2007 | Sicvol et al. | |
| 7,186,255 B2 * | 3/2007 | Baynham | A61B 17/7035 606/266 |
| 7,188,626 B2 | 3/2007 | Foley et al. | |
| 7,211,087 B2 | 5/2007 | Young | |
| 7,250,052 B2 | 7/2007 | Landry et al. | |
| 7,261,714 B2 | 8/2007 | Richelsoph | |
| 7,270,665 B2 | 9/2007 | Morrison et al. | |
| 7,282,064 B2 | 10/2007 | Chin | |
| 7,303,562 B2 * | 12/2007 | Cavagna | A61B 17/701 606/86 A |
| 7,306,603 B2 | 12/2007 | Boehm, Jr. et al. | |
| 7,371,239 B2 | 5/2008 | Dec et al. | |
| 7,422,597 B1 | 9/2008 | Alby | |
| 7,442,597 B2 | 10/2008 | Tsui et al. | |
| 7,455,685 B2 | 11/2008 | Justis | |
| 7,462,182 B2 | 12/2008 | Lim | |
| 7,465,306 B2 | 12/2008 | Pond, Jr. et al. | |
| 7,470,279 B2 | 12/2008 | Jackson | |
| 7,476,240 B2 | 1/2009 | Raymond et al. | |
| 7,491,207 B2 | 2/2009 | Keyer et al. | |
| 7,491,208 B2 | 2/2009 | Pond et al. | |
| 7,491,218 B2 | 2/2009 | Landry et al. | |
| 7,497,869 B2 * | 3/2009 | Justis | A61B 17/7002 606/279 |
| 7,520,879 B2 | 4/2009 | Justis et al. | |
| 7,527,638 B2 | 5/2009 | Anderson et al. | |
| 7,547,318 B2 | 6/2009 | Birkmeyer et al. | |
| 7,563,264 B2 | 7/2009 | Landry et al. | |
| 7,572,276 B2 | 8/2009 | Lim et al. | |
| 7,597,694 B2 | 10/2009 | Lim et al. | |
| 7,608,081 B2 | 10/2009 | Abdelgany | |
| 7,608,096 B2 | 10/2009 | Foley et al. | |
| 7,618,424 B2 * | 11/2009 | Wilcox | A61B 17/025 606/105 |
| 7,621,918 B2 | 11/2009 | Jackson | |
| 7,648,522 B2 | 1/2010 | David | |
| 7,651,502 B2 | 1/2010 | Jackson | |
| 7,651,516 B2 | 1/2010 | Petit et al. | |
| 7,666,189 B2 | 2/2010 | Gerber et al. | |
| 7,678,112 B2 | 3/2010 | Rezach | |
| 7,678,136 B2 | 3/2010 | Doubler et al. | |
| 7,686,809 B2 | 3/2010 | Triplett et al. | |
| 7,691,132 B2 | 4/2010 | Landry et al. | |
| 7,704,270 B2 | 4/2010 | DeConinck | |
| 7,708,763 B2 | 5/2010 | Selover et al. | |
| 7,717,944 B2 | 5/2010 | Foley et al. | |
| 7,722,645 B2 | 5/2010 | Bryan | |
| 7,744,635 B2 | 6/2010 | Sweeney et al. | |
| 7,753,940 B2 | 7/2010 | Veldman et al. | |
| 7,758,584 B2 * | 7/2010 | Bankoski et al. | 606/104 |
| 7,763,047 B2 | 7/2010 | Ritland | |
| 7,763,054 B2 | 7/2010 | Clement et al. | |
| 7,763,055 B2 | 7/2010 | Foley | |
| 7,776,040 B2 | 8/2010 | Markworth et al. | |
| 7,776,051 B2 | 8/2010 | Colleran et al. | |
| 7,789,897 B2 | 9/2010 | Sanders | |
| 7,799,059 B2 | 9/2010 | Kramer et al. | |
| 7,811,288 B2 | 10/2010 | Jones et al. | |
| 7,815,664 B2 | 10/2010 | Sherman et al. | |
| 7,819,902 B2 | 10/2010 | Abdelgany et al. | |
| 7,824,411 B2 | 11/2010 | Varieur et al. | |
| 7,824,413 B2 | 11/2010 | Varieur et al. | |
| 7,837,715 B2 | 11/2010 | Petit et al. | |
| 7,842,044 B2 | 11/2010 | Runco et al. | |
| 7,842,073 B2 | 11/2010 | Richelsoph et al. | |
| 7,850,715 B2 | 12/2010 | Banouskou et al. | |
| 7,850,716 B2 | 12/2010 | Taylor | |
| 7,850,719 B2 | 12/2010 | Gournay et al. | |
| 7,854,751 B2 | 12/2010 | Sicvol et al. | |
| 7,862,587 B2 | 1/2011 | Jackson | |
| 7,862,595 B2 | 1/2011 | Foley et al. | |
| 7,867,259 B2 | 1/2011 | Foley et al. | |
| 7,887,539 B2 | 2/2011 | Dunbar, Jr. et al. | |
| 7,896,902 B2 | 3/2011 | Jeon et al. | |
| 7,914,558 B2 | 3/2011 | Landry et al. | |
| 7,918,792 B2 * | 4/2011 | Drzyzga | A61B 1/32 600/215 |
| 7,931,677 B2 | 4/2011 | Abdelgany | |
| 7,955,355 B2 | 6/2011 | Chin | |
| 7,955,363 B2 | 6/2011 | Richelsoph | |
| 7,976,569 B2 | 7/2011 | Justis | |
| 7,985,242 B2 | 7/2011 | Forton et al. | |
| 8,002,798 B2 | 8/2011 | Chin et al. | |
| 8,021,398 B2 | 9/2011 | Sweeney et al. | |
| 8,029,546 B2 | 10/2011 | Capote et al. | |
| 8,034,084 B2 | 10/2011 | Landry et al. | |
| 8,043,343 B2 * | 10/2011 | Miller et al. | 606/279 |
| 8,066,739 B2 | 11/2011 | Jackson | |
| 8,075,592 B2 | 12/2011 | Landry et al. | |
| 8,088,152 B2 | 1/2012 | Schumacher | |
| 8,092,494 B2 * | 1/2012 | Butler et al. | 606/246 |
| 8,096,996 B2 | 1/2012 | Gutierrez et al. | |
| 8,097,027 B2 | 1/2012 | Lim et al. | |
| 8,100,828 B2 * | 1/2012 | Frey et al. | 600/234 |
| 8,100,913 B2 | 1/2012 | Abdelgany | |
| 8,100,915 B2 | 1/2012 | Jackson | |
| 8,100,951 B2 | 1/2012 | Justis et al. | |
| 8,105,361 B2 | 1/2012 | Anderson et al. | |
| 8,118,737 B2 * | 2/2012 | Perez-Cruet et al. | 600/210 |
| 8,123,751 B2 * | 2/2012 | Shluzas | 606/86 R |
| 8,128,665 B2 | 3/2012 | Banouskou et al. | |
| 8,152,810 B2 | 4/2012 | Jackson | |
| 8,172,855 B2 * | 5/2012 | Abdou | 606/99 |
| 8,177,817 B2 | 5/2012 | Fallin | |
| 8,221,472 B2 | 7/2012 | Peterson et al. | |
| 8,262,662 B2 | 9/2012 | Beardsley et al. | |
| 8,262,702 B2 | 9/2012 | Giger et al. | |
| 8,287,546 B2 | 10/2012 | King et al. | |
| 8,292,892 B2 | 10/2012 | Jackson | |
| 8,317,796 B2 | 11/2012 | Stihl et al. | |
| 8,357,184 B2 * | 1/2013 | Woolley | A61B 17/0206 600/210 |
| 8,460,308 B2 | 6/2013 | Marino et al. | |
| 8,469,960 B2 | 6/2013 | Hutton et al. | |
| 8,480,713 B2 | 7/2013 | Rezach | |
| 8,518,082 B2 | 8/2013 | Sicvol et al. | |
| 8,535,318 B2 | 9/2013 | Peterson et al. | |
| 8,585,741 B2 | 11/2013 | Gabelberger et al. | |
| 8,679,129 B2 | 3/2014 | Sorrenti et al. | |
| 9,314,274 B2 | 4/2016 | Amstutz et al. | |

(56) References Cited

U.S. PATENT DOCUMENTS

| | | |
|---|---|---|
| 9,402,663 B2 | 8/2016 | Peterson et al. |
| 2002/0020255 A1 | 2/2002 | Simon et al. |
| 2002/0035367 A1 | 3/2002 | Ritland |
| 2002/0107519 A1 | 8/2002 | Dixon et al. |
| 2002/0193802 A1 | 12/2002 | Zdeblick et al. |
| 2003/0040752 A1 | 2/2003 | Kitchens |
| 2003/0073998 A1 | 4/2003 | Pagliuca et al. |
| 2003/0135220 A1 | 7/2003 | Cauthen |
| 2003/0149341 A1 | 8/2003 | Clifton |
| 2003/0149438 A1 | 8/2003 | Nichols et al. |
| 2003/0191371 A1 | 10/2003 | Smith et al. |
| 2003/0199872 A1 | 10/2003 | Markworth et al. |
| 2003/0208203 A1 | 11/2003 | Lim et al. |
| 2003/0216768 A1 | 11/2003 | Gitis et al. |
| 2003/0225408 A1 | 12/2003 | Nichols et al. |
| 2003/0236447 A1 | 12/2003 | Ritland |
| 2004/0002629 A1 | 1/2004 | Branch et al. |
| 2004/0024398 A1 | 2/2004 | Hovda et al. |
| 2004/0034351 A1 | 2/2004 | Sherman et al. |
| 2004/0039384 A1 | 2/2004 | Boehm et al. |
| 2004/0092930 A1 | 5/2004 | Petit et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147937 A1 | 7/2004 | Dunbar et al. |
| 2004/0153068 A1 | 8/2004 | Janowski et al. |
| 2004/0172022 A1 | 9/2004 | Landry et al. |
| 2004/0176763 A1 | 9/2004 | Foley et al. |
| 2004/0215190 A1 | 10/2004 | Nguyen et al. |
| 2004/0254574 A1 | 12/2004 | Morrison et al. |
| 2004/0267275 A1 | 12/2004 | Cournoyer et al. |
| 2005/0004593 A1 | 1/2005 | Simonson |
| 2005/0010220 A1 | 1/2005 | Casutt et al. |
| 2005/0021031 A1 | 1/2005 | Foley et al. |
| 2005/0021040 A1 | 1/2005 | Bertagnoli |
| 2005/0036244 A1 | 2/2005 | Carey et al. |
| 2005/0038432 A1 | 2/2005 | Shaolian et al. |
| 2005/0038433 A1 | 2/2005 | Young |
| 2005/0065517 A1 | 3/2005 | Chin |
| 2005/0065518 A1 | 3/2005 | Michelson |
| 2005/0070765 A1 | 3/2005 | Abdelgany et al. |
| 2005/0070901 A1 | 3/2005 | David |
| 2005/0074445 A1 | 4/2005 | Papas et al. |
| 2005/0075644 A1 | 4/2005 | DiPoto et al. |
| 2005/0080418 A1 | 4/2005 | Simonson et al. |
| 2005/0085813 A1 | 4/2005 | Spitler et al. |
| 2005/0090824 A1 | 4/2005 | Shluzas et al. |
| 2005/0096654 A1 | 5/2005 | Lin |
| 2005/0131408 A1 | 6/2005 | Sicvol et al. |
| 2005/0131419 A1 | 6/2005 | McCord et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0159650 A1 | 7/2005 | Raymond et al. |
| 2005/0171540 A1 | 8/2005 | Lim et al. |
| 2005/0182410 A1 | 8/2005 | Jackson |
| 2005/0192570 A1 | 9/2005 | Jackson |
| 2005/0192579 A1 | 9/2005 | Jackson |
| 2005/0192589 A1 | 9/2005 | Raymond et al. |
| 2005/0203532 A1* | 9/2005 | Ferguson ............. A61B 17/025 606/90 |
| 2005/0215999 A1 | 9/2005 | Birkmeyer et al. |
| 2005/0228380 A1 | 10/2005 | Moore et al. |
| 2005/0228382 A1 | 10/2005 | Richelsoph et al. |
| 2005/0228400 A1 | 10/2005 | Chao et al. |
| 2005/0234449 A1 | 10/2005 | Aferzon |
| 2005/0240181 A1* | 10/2005 | Boomer et al. ................. 606/61 |
| 2005/0277934 A1 | 12/2005 | Vardiman |
| 2006/0009780 A1 | 1/2006 | Foley et al. |
| 2006/0025768 A1 | 2/2006 | Iott et al. |
| 2006/0036244 A1 | 2/2006 | Spitler et al. |
| 2006/0036252 A1 | 2/2006 | Baynham et al. |
| 2006/0036255 A1 | 2/2006 | Pond et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0074445 A1 | 4/2006 | Gerber et al. |
| 2006/0079894 A1* | 4/2006 | Colleran et al. ................. 606/61 |
| 2006/0079909 A1 | 4/2006 | Runco et al. |
| 2006/0084993 A1 | 4/2006 | Landry et al. |
| 2006/0095035 A1 | 5/2006 | Jones et al. |
| 2006/0106380 A1 | 5/2006 | Colleran et al. |
| 2006/0106394 A1 | 5/2006 | Colleran |
| 2006/0111712 A1 | 5/2006 | Jackson |
| 2006/0111713 A1 | 5/2006 | Jackson |
| 2006/0111714 A1 | 5/2006 | Foley et al. |
| 2006/0111715 A1 | 5/2006 | Jackson |
| 2006/0122597 A1 | 6/2006 | Jones et al. |
| 2006/0136380 A1 | 6/2006 | Purcell |
| 2006/0142716 A1 | 6/2006 | Long et al. |
| 2006/0142761 A1 | 6/2006 | Landry et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0184172 A1 | 8/2006 | Michelson et al. |
| 2006/0184178 A1 | 8/2006 | Jackson |
| 2006/0200135 A1 | 9/2006 | Sherman et al. |
| 2006/0206114 A1 | 9/2006 | Ensign et al. |
| 2006/0229614 A1 | 10/2006 | Foley et al. |
| 2006/0241596 A1 | 10/2006 | Rezach |
| 2006/0241601 A1 | 10/2006 | Trautwein et al. |
| 2006/0241649 A1 | 10/2006 | Vasta et al. |
| 2006/0247624 A1 | 11/2006 | Banouskou et al. |
| 2006/0247658 A1 | 11/2006 | Pond et al. |
| 2006/0253118 A1 | 11/2006 | Bailey |
| 2006/0264942 A1 | 11/2006 | Lim et al. |
| 2006/0264962 A1 | 11/2006 | Chin et al. |
| 2006/0276803 A1 | 12/2006 | Salerni |
| 2006/0293678 A1 | 12/2006 | Davison et al. |
| 2006/0293680 A1 | 12/2006 | Jackson |
| 2006/0293693 A1* | 12/2006 | Farr et al. ................. 606/104 |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016200 A1 | 1/2007 | Jackson |
| 2007/0025132 A1 | 2/2007 | Liaw |
| 2007/0032162 A1 | 2/2007 | Jackson |
| 2007/0073294 A1 | 3/2007 | Chin et al. |
| 2007/0083210 A1* | 4/2007 | Hestad ............. A61B 17/17 606/86 R |
| 2007/0106123 A1 | 5/2007 | Gorek et al. |
| 2007/0129731 A1 | 6/2007 | Sicvol et al. |
| 2007/0135817 A1 | 6/2007 | Ensign |
| 2007/0161987 A1 | 7/2007 | Capote et al. |
| 2007/0161998 A1 | 7/2007 | Whipple |
| 2007/0162046 A1 | 7/2007 | Vandewalle |
| 2007/0167946 A1 | 7/2007 | Triplett et al. |
| 2007/0167954 A1 | 7/2007 | Sicvol et al. |
| 2007/0173745 A1 | 7/2007 | Diederich et al. |
| 2007/0185491 A1 | 8/2007 | Foley et al. |
| 2007/0198015 A1 | 8/2007 | Foley et al. |
| 2007/0233067 A1 | 10/2007 | Taylor |
| 2007/0233079 A1 | 10/2007 | Fallin et al. |
| 2007/0238335 A1 | 10/2007 | Veldman et al. |
| 2007/0260125 A1* | 11/2007 | Strauss ............. A61B 1/32 600/219 |
| 2007/0270842 A1* | 11/2007 | Bankoski et al. ............. 606/61 |
| 2007/0276803 A1 | 11/2007 | Shakib et al. |
| 2008/0005174 A1 | 1/2008 | Stephenson |
| 2008/0009864 A1 | 1/2008 | Forton et al. |
| 2008/0039838 A1 | 2/2008 | Landry et al. |
| 2008/0045957 A1 | 2/2008 | Landry et al. |
| 2008/0051794 A1* | 2/2008 | Dec et al. ................. 606/73 |
| 2008/0051897 A1 | 2/2008 | Lopez et al. |
| 2008/0077139 A1 | 3/2008 | Landry et al. |
| 2008/0077155 A1 | 3/2008 | Diederich et al. |
| 2008/0081951 A1* | 4/2008 | Frasier ............. A61B 17/0218 600/207 |
| 2008/0086132 A1* | 4/2008 | Biedermann et al. ............. 606/61 |
| 2008/0091213 A1 | 4/2008 | Jackson |

(56) References Cited

U.S. PATENT DOCUMENTS

| | | | |
|---|---|---|---|
| 2008/0140132 A1* | 6/2008 | Perez-Cruet | A61B 17/7032 606/301 |
| 2008/0154278 A1 | 6/2008 | Abdelgany | |
| 2008/0167688 A1 | 7/2008 | Fauth et al. | |
| 2008/0177270 A1 | 7/2008 | Sorrenti et al. | |
| 2008/0255567 A1 | 10/2008 | Accordino | |
| 2008/0262318 A1* | 10/2008 | Gorek et al. | 600/235 |
| 2008/0288005 A1 | 11/2008 | Jackson | |
| 2008/0294198 A1 | 11/2008 | Jackson | |
| 2008/0294202 A1 | 11/2008 | Peterson et al. | |
| 2008/0300638 A1 | 12/2008 | Beardsley et al. | |
| 2009/0005814 A1* | 1/2009 | Miller | A61B 17/7037 606/246 |
| 2009/0088604 A1* | 4/2009 | Lowry | A61B 17/02 600/210 |
| 2009/0093684 A1* | 4/2009 | Schorer | 600/210 |
| 2009/0138056 A1 | 5/2009 | Anderson et al. | |
| 2009/0163924 A1 | 6/2009 | Justis | |
| 2009/0171391 A1 | 7/2009 | Hutton et al. | |
| 2009/0228052 A1 | 9/2009 | Beardsley et al. | |
| 2009/0228055 A1 | 9/2009 | Jackson | |
| 2009/0228056 A1 | 9/2009 | Jackson | |
| 2009/0264926 A1 | 10/2009 | Taylor et al. | |
| 2009/0270916 A1* | 10/2009 | Ramsay et al. | 606/246 |
| 2009/0287253 A1 | 11/2009 | Felix et al. | |
| 2009/0318972 A1 | 12/2009 | Jackson | |
| 2009/0326585 A1 | 12/2009 | Baccelli et al. | |
| 2010/0024487 A1 | 2/2010 | Khoo et al. | |
| 2010/0030283 A1 | 2/2010 | King et al. | |
| 2010/0036443 A1 | 2/2010 | Hutton et al. | |
| 2010/0049253 A1 | 2/2010 | Miller | |
| 2010/0063546 A1 | 3/2010 | Miller et al. | |
| 2010/0094346 A1 | 4/2010 | Matityahu | |
| 2010/0131016 A1 | 5/2010 | Gerber et al. | |
| 2010/0168796 A1 | 7/2010 | Eliasen et al. | |
| 2010/0174325 A1 | 7/2010 | Won et al. | |
| 2010/0198272 A1 | 8/2010 | Keyer et al. | |
| 2010/0241171 A1 | 9/2010 | Clement et al. | |
| 2010/0268279 A1 | 10/2010 | Gabelberger et al. | |
| 2010/0268284 A1 | 10/2010 | Bankoski et al. | |
| 2010/0274252 A1 | 10/2010 | Bottomley et al. | |
| 2010/0331849 A1 | 12/2010 | Riesinger et al. | |
| 2011/0054537 A1 | 3/2011 | Miller et al. | |
| 2011/0130634 A1 | 6/2011 | Solitario, Jr. et al. | |
| 2011/0166606 A1 | 7/2011 | Stihl et al. | |
| 2011/0184465 A1* | 7/2011 | Boehm | A61B 17/7005 606/264 |
| 2011/0184469 A1 | 7/2011 | Ballard et al. | |
| 2011/0263945 A1 | 10/2011 | Peterson | |
| 2012/0089191 A1 | 4/2012 | Altarac et al. | |
| 2012/0290012 A1 | 11/2012 | Rutledge | |
| 2012/0303062 A1 | 11/2012 | Guetlin | |
| 2013/0253598 A1 | 9/2013 | Jackson | |
| 2013/0274804 A1 | 10/2013 | Hutton et al. | |
| 2013/0331892 A1 | 12/2013 | Solitario, Jr. | |
| 2014/0012321 A1 | 1/2014 | Hutton et al. | |
| 2014/0074171 A1 | 3/2014 | Hutton et al. | |
| 2014/0114360 A1 | 4/2014 | Gephart et al. | |
| 2016/0199100 A1 | 7/2016 | Amstutz et al. | |

FOREIGN PATENT DOCUMENTS

| | | |
|---|---|---|
| CN | 1913836 A | 2/2007 |
| DE | 9215561 | 1/1993 |
| DE | 4238339 | 5/1994 |
| DE | 19726754 | 2/1999 |
| DE | 10027988 | 1/2002 |
| EP | 0528177 | 2/1993 |
| EP | 0558883 | 9/1993 |
| EP | 0483242 B1 | 5/1995 |
| EP | 0836835 | 4/1998 |
| EP | 0885598 | 12/1998 |
| EP | 0947174 | 10/1999 |
| EP | 0938872 B1 | 7/2002 |
| EP | 0746255 B1 | 9/2002 |
| EP | 0814716 B1 | 7/2003 |
| EP | 0981301 B1 | 8/2003 |
| EP | 0934027 B1 | 12/2003 |
| EP | 0814713 B1 | 2/2004 |
| EP | 1392190 | 3/2004 |
| EP | 1087711 B1 | 5/2004 |
| EP | 0934028 B1 | 6/2004 |
| EP | 1196102 B1 | 9/2004 |
| EP | 1459215 | 9/2004 |
| EP | 1214006 B1 | 10/2005 |
| EP | 1316295 B1 | 10/2005 |
| EP | 1330196 B1 | 10/2005 |
| EP | 1119304 B1 | 12/2005 |
| EP | 1317215 B1 | 12/2005 |
| EP | 1642542 | 4/2006 |
| EP | 0986338 B1 | 7/2006 |
| EP | 1248573 B1 | 8/2006 |
| EP | 1635722 B1 | 6/2008 |
| EP | 1708630 B1 | 11/2009 |
| FR | 2757761 | 7/1998 |
| JP | 11076247 | 3/1999 |
| JP | 2000-032359 A | 1/2000 |
| JP | 2001-507259 A | 6/2001 |
| JP | 2004-512134 A | 4/2004 |
| JP | 2004-516040 A | 6/2004 |
| JP | 2006-504505 A | 2/2006 |
| JP | 2007-532258 A | 11/2007 |
| JP | 2010-533547 A | 10/2010 |
| JP | 2012-501809 A | 1/2012 |
| KR | 10-2009-0005316 A | 1/2009 |
| WO | 91/01115 A1 | 2/1991 |
| WO | WO 95/14437 | 6/1995 |
| WO | 96/27340 A1 | 9/1996 |
| WO | 96/28104 A1 | 9/1996 |
| WO | 98/12976 A1 | 4/1998 |
| WO | 98/12977 A1 | 4/1998 |
| WO | 98/34554 A1 | 8/1998 |
| WO | 01/52758 A1 | 7/2001 |
| WO | 02/02022 A1 | 1/2002 |
| WO | 02/22030 A2 | 3/2002 |
| WO | 02/36026 A2 | 5/2002 |
| WO | 02/94114 A1 | 11/2002 |
| WO | WO 03/052634 | 6/2003 |
| WO | 00/19923 A1 | 4/2004 |
| WO | 2004/041100 A1 | 5/2004 |
| WO | WO 2004/058082 | 7/2004 |
| WO | 2005/020829 A1 | 3/2005 |
| WO | 2005/058141 A2 | 6/2005 |
| WO | WO 2005/060534 | 7/2005 |
| WO | 2005/072632 A1 | 8/2005 |
| WO | 2005/104970 A1 | 11/2005 |
| WO | 2006/042188 A2 | 4/2006 |
| WO | WO 2006/060430 | 6/2006 |
| WO | 2006/116305 A1 | 11/2006 |
| WO | WO 2006/116662 | 11/2006 |
| WO | 2007/022790 A1 | 3/2007 |
| WO | WO 2007/025132 | 3/2007 |
| WO | 2007/038350 A2 | 4/2007 |
| WO | WO 2007/067443 | 6/2007 |
| WO | WO 2007/070757 | 6/2007 |
| WO | 2007/117366 A2 | 10/2007 |
| WO | WO 2007/121271 | 10/2007 |
| WO | WO 2007/146833 | 12/2007 |
| WO | 2008/014477 A1 | 1/2008 |
| WO | 2008/022268 A2 | 2/2008 |
| WO | WO 2009/011929 A1 | 1/2009 |
| WO | WO 2009/014540 | 1/2009 |
| WO | 2009/055026 A1 | 4/2009 |
| WO | 2009/133539 A1 | 11/2009 |
| WO | 2010/030916 A2 | 3/2010 |
| WO | 2010/103198 A1 | 9/2010 |

(56) References Cited

FOREIGN PATENT DOCUMENTS

| WO | 2010/150140 A1 | 12/2010 |
|----|----------------|---------|
| WO | 2011/012690 A1 | 2/2011  |

OTHER PUBLICATIONS

Aperture™, "Spinal Access System", DePuy AcroMed, 2003, 6 pages.
Atavi™, "Atraumatic Spine Fusion System—Endoscopic Posterolateral Fusion", Endius, 2001, 10 pages.
Branch et al., "Tangent: Posterior Impacted Instrument Set Technique", Medtronic Sofamor Danek, 2000, 17 pages.
Foley et al., "Cd Horizon Sextant Rod Insertion System Surgical Technique", Medtronic Sofamor Danek, 2002, 30 pages.
Harms, "Polyaxial Reduction Screw: Surgical Technique", Depuy AcroMed, 1998, 13 pages.
Hilton et al., "Metr$_x$: Microdiscectomy Surgical Technique", Medtronic Sofamor Danek, 2002, 20 pages.
Kambin, "The Role of Minimally Invasive Surgery in Spinal Disorders", Advances in Operative Orthopedics, 1995, 3, 147-171.
Muller et al., "Techniques and Applications : A Keyhole Approach for Endoscopically assisted Pedicle Screw Fixation in Lumbar Spine Inability", Jul. 2000 Neurosurgery, 47(1), 11 pages.
Synthes Spine, "Constellation CP System: A Minimally Invasive System for use with Cannulated Pangea", Technique Guide, Synthes Spinem, 2008, 42 pages.
Thongtrangan et al., "Minimally Invasive Spinal Surgery: A Historical Perspective", Neurosurg Focus, Jan. 2004, 16(1), article 13, 9 pages.
Turner et al., "A New Radially Expanding Access System for Laparoscopic Procedures versus Conventional Cannulas", The Journal of the American Association of Gynecologic Laparoscopists, Aug. 1996, 3(4), 7 pages.
Wiltse et al., "New Uses and Refinements of the Paraspinal Approach to the Lumbar Spine" Jan. 18, 1988, 22 pages.
Viper 2 System Guide, DePuy Spine, 2011, 60 pages.
Synthes Spine, "USS Fracture System: Technique Guide", 2001, 20 pages.
Muller, et al., "A Keyhole Approach for Endoscopically Assisted Pedicle Screw Fixation in Lumbar Spine Instability [Techniques and Applications]", Department of Neurosurgery, 18 pages, Received, Sep. 14, 1999, Accepted Mar. 2, 2000.
Matrix Spine System—Deformity Technique Guide, "A Posterior Pedicle Screw, Hook, and Rod Fixation System," Synthes, copyrights 2010, 75 pages.
International Patent Application No. PCT/US2007/066469: International Search Report dated Aug. 1, 2008, 6 pages.

* cited by examiner

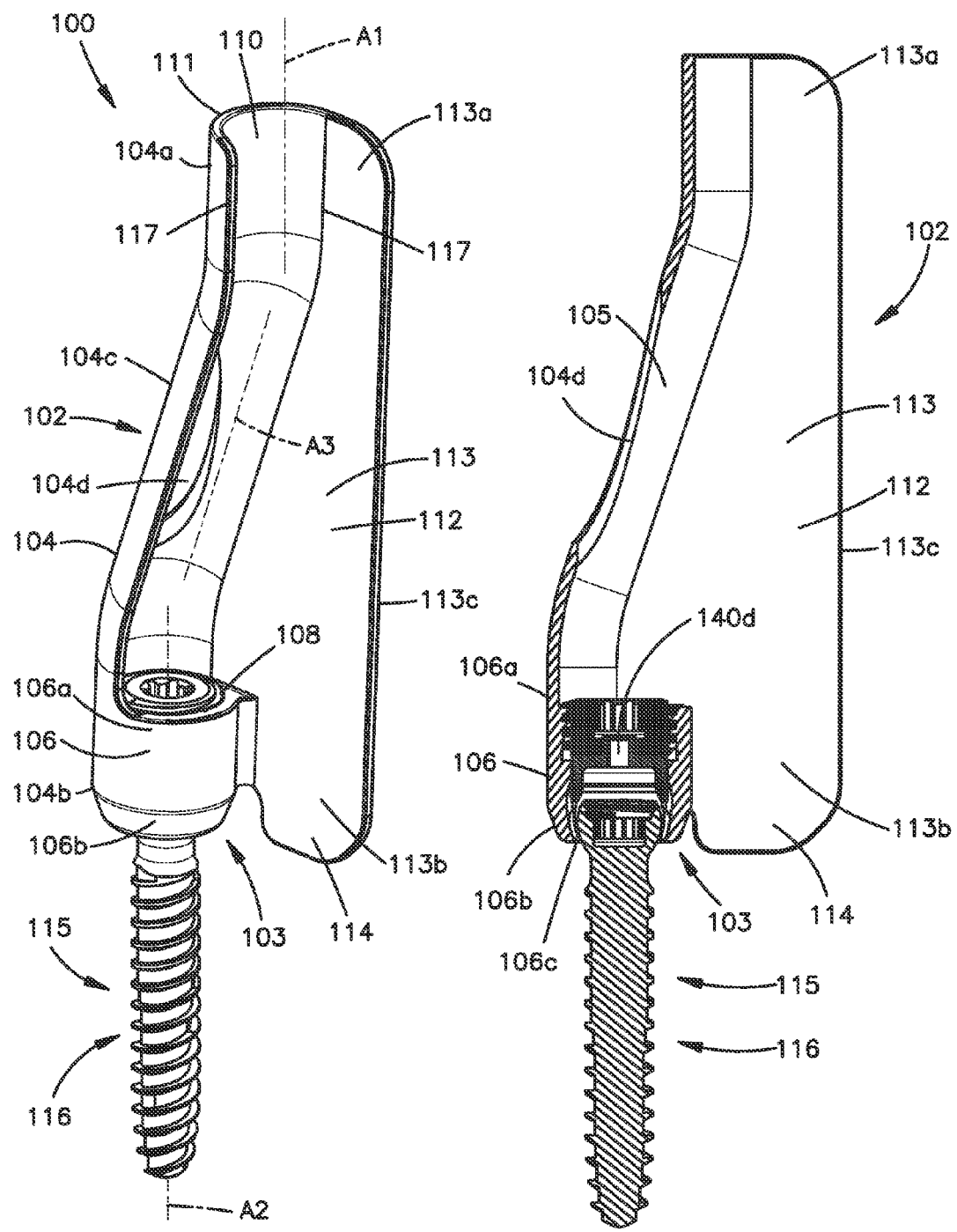

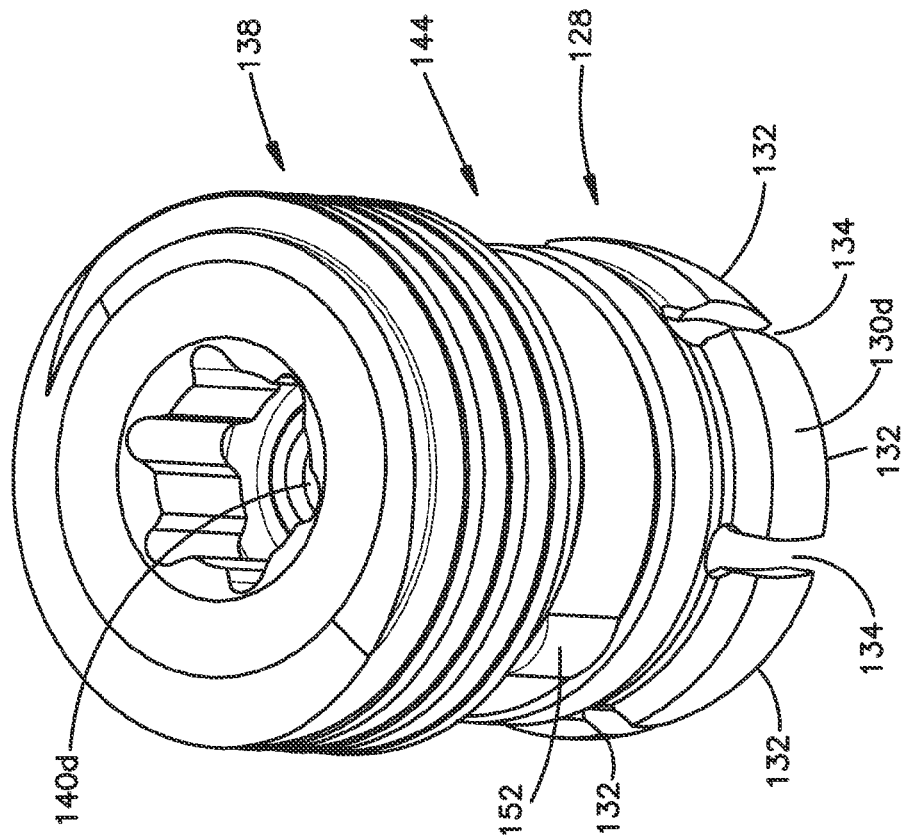
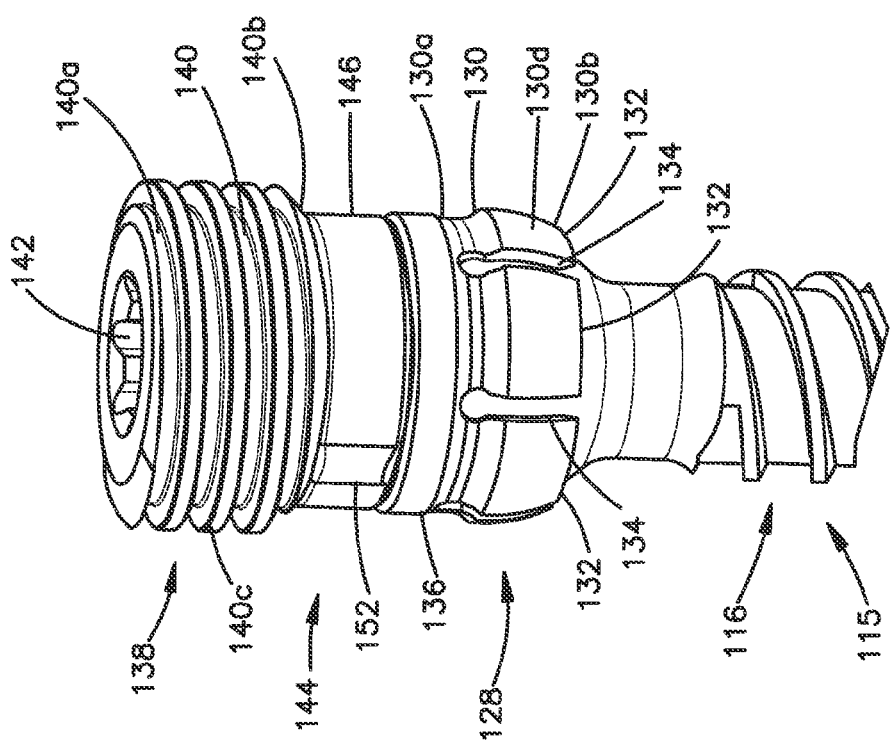

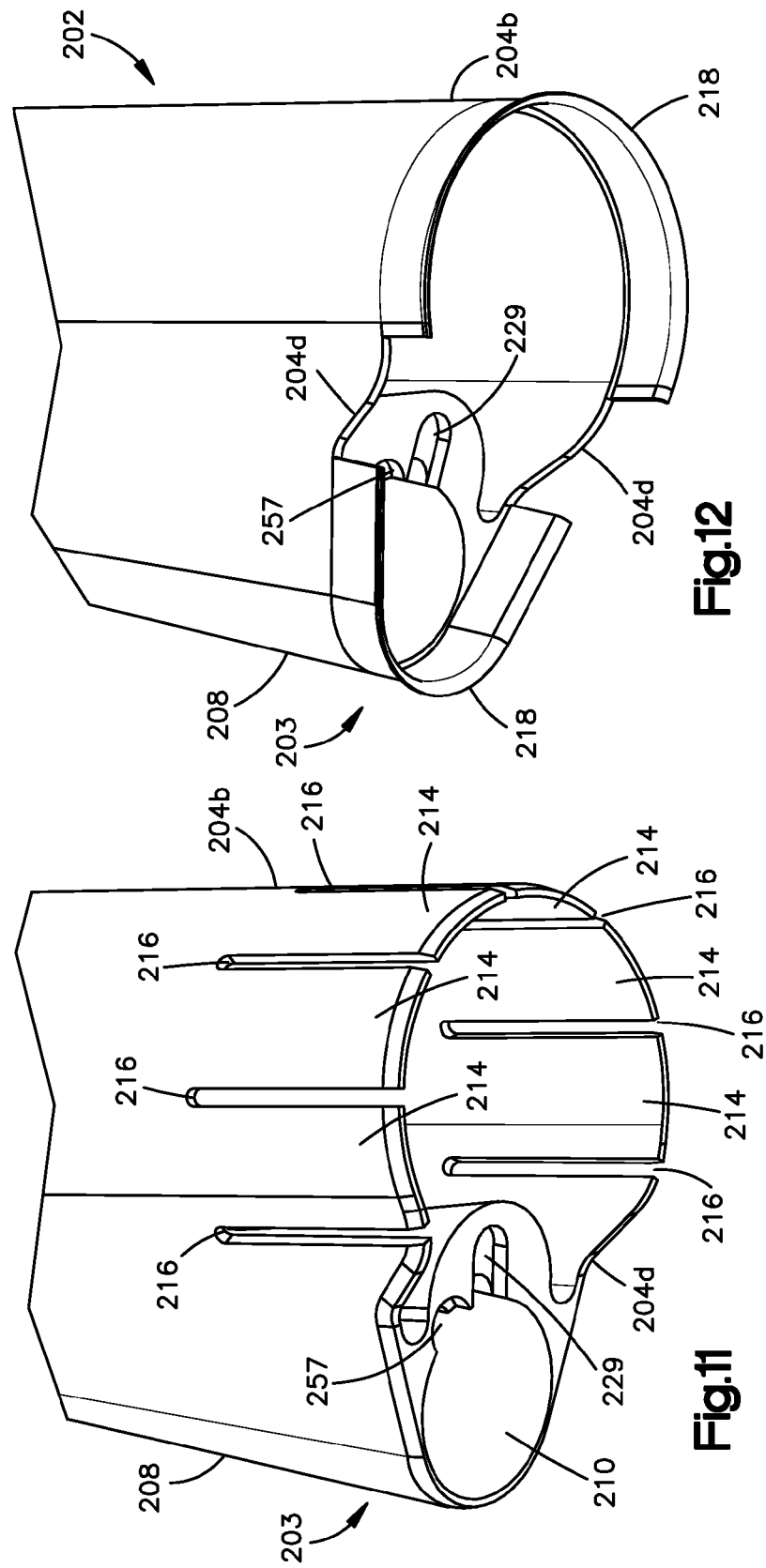

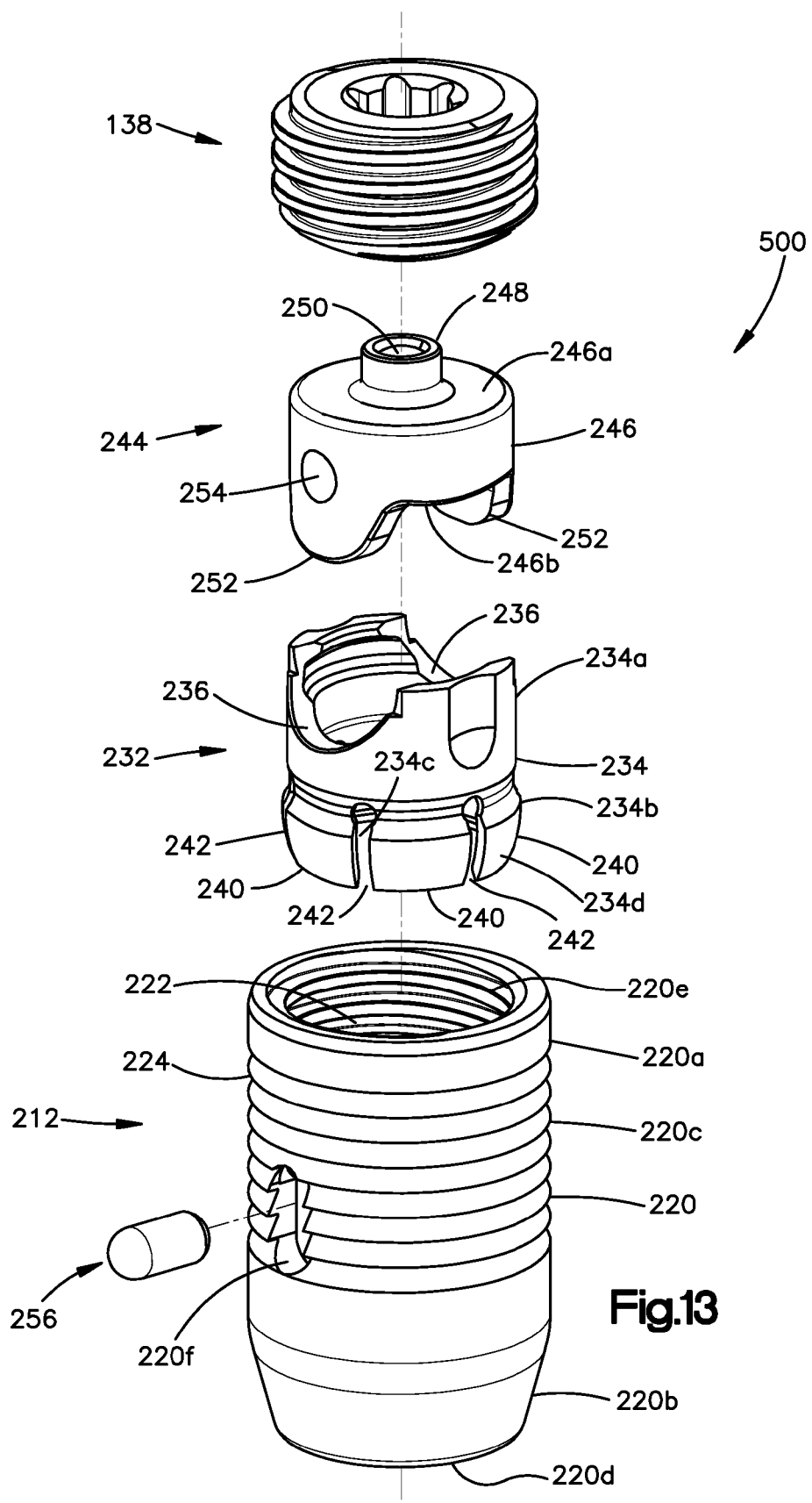

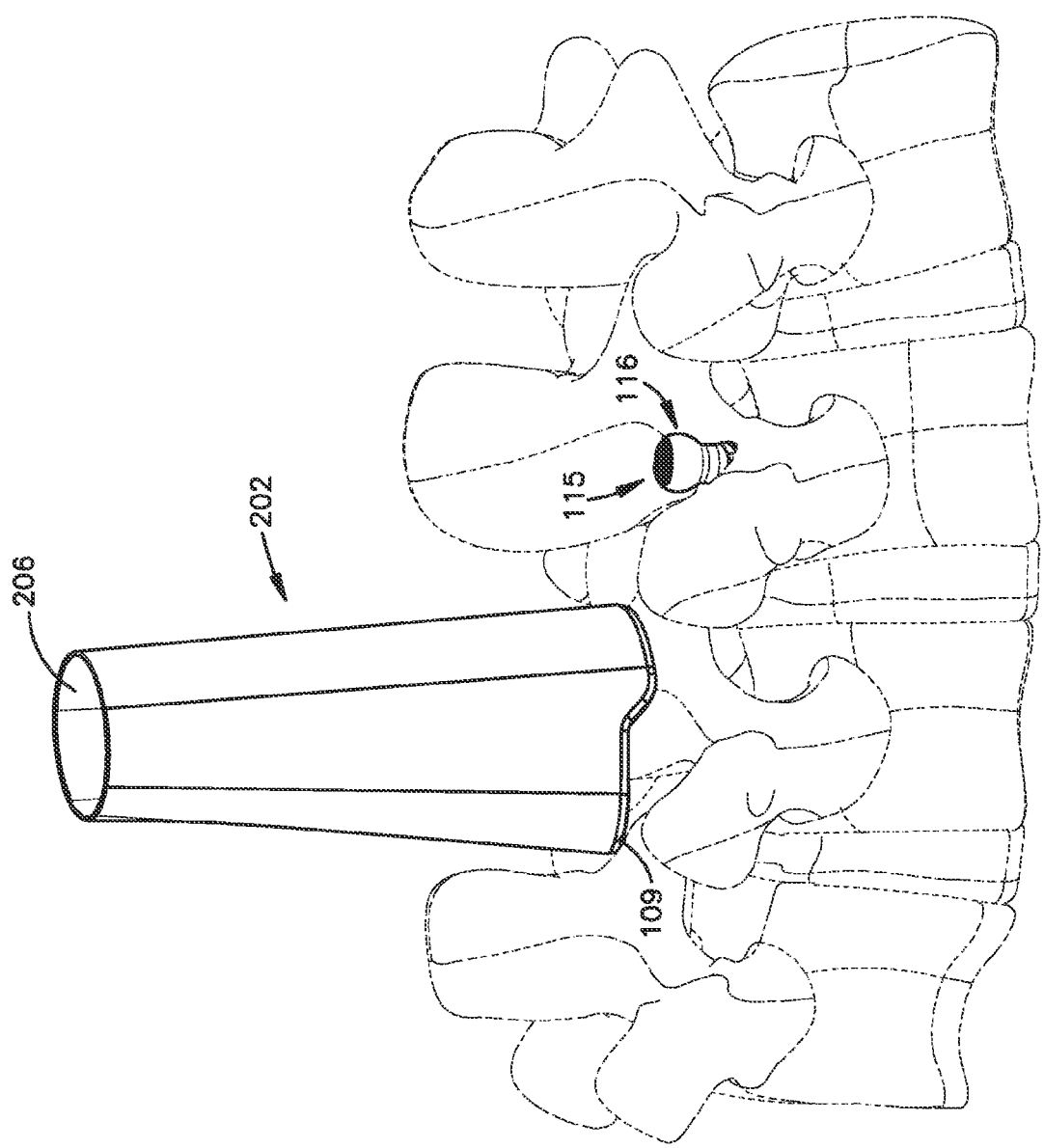

PATIENT-MOUNTED RETRACTION

CROSS-REFERENCE TO RELATED APPLICATIONS

This patent application claims priority to U.S. provisional patent application No. 61/179,924, filed May 20, 2009, which is incorporated herein by reference in its entirety.

TECHNICAL FIELD

The present disclosure relates generally to surgery, and in particular relates to patient-mounted retraction apparatuses and associated surgical methods and procedures for using same.

BACKGROUND

Retractors and/or cannulas may be used to provide a surgeon with an access portal to a surgical site in a patient's body. Various minimally invasive procedures, including spinal procedures such as decompression, fusion, external fixation, and the like may be performed through such access portals.

The retractors and/or cannulas typically used in these procedures must often be secured in position within a surgical site via external devices mounted to the operating table, for example via an adjustable arm coupled to a table mounted retractor frame. The setup, deployment, positioning, and repositioning of these devices before and during surgery can be awkward and time-consuming. Furthermore, the arms, frames, and other components associated with these table mounted retraction devices typically crowd the area around the surgical site, thereby reducing the space a surgeon has in which to operate, limiting the flexibility the surgeon has in his choice of instrumentation and/or hardware to accomplish a procedure, and impeding intra-operative imaging.

SUMMARY

In accordance with one embodiment, a retractor body with an anchor receptacle disposed at its distal end is provided. The anchor receptacle carries a locking assembly that is configured to connect the retractor body onto a bone anchor. The bone anchor is configured to be driven into an underlying target location of a patient.

BRIEF DESCRIPTION OF THE DRAWINGS

The foregoing summary, as well as the following detailed description of embodiments of the application, will be better understood when read in conjunction with the appended drawings. For the purposes of illustrating the patient-mounted retraction systems and methods of the present application, there are shown in the drawings preferred embodiments. It should be understood, however, that the instant application is not limited to the precise arrangements and/or instrumentalities illustrated in the drawings, in which:

FIG. 1 is a perspective view of a blade type patient-mounted retractor assembly in accordance with an embodiment;

FIG. 2 is a cross sectional view of the blade type patient-mounted retractor assembly illustrated in FIG. 1;

FIG. 4 is a perspective view of the locking cap, the intermediate wedge, the collet, and the bone anchor illustrated in FIG. 3 in an assembled configuration;

FIG. 5 is a perspective view of the locking cap, the intermediate wedge, and the collet illustrated in FIG. 3, in an assembled configuration;

FIG. 11 is a perspective view of a distal end of the tube type patient-mounted retractor illustrated in FIG. 10;

FIG. 12 is a perspective view of flexible skirting affixed to the distal end of the tube type patient-mounted retractor illustrated in FIG. 11;

FIG. 13 is an exploded assembly view of an anchor cartridge in accordance with an embodiment;

FIG. 16 is a perspective view of a tube type patient-mounted retractor assembly disposed in a surgical site in accordance with an embodiment;

DETAILED DESCRIPTION OF ILLUSTRATIVE EMBODIMENTS

Figure 3:
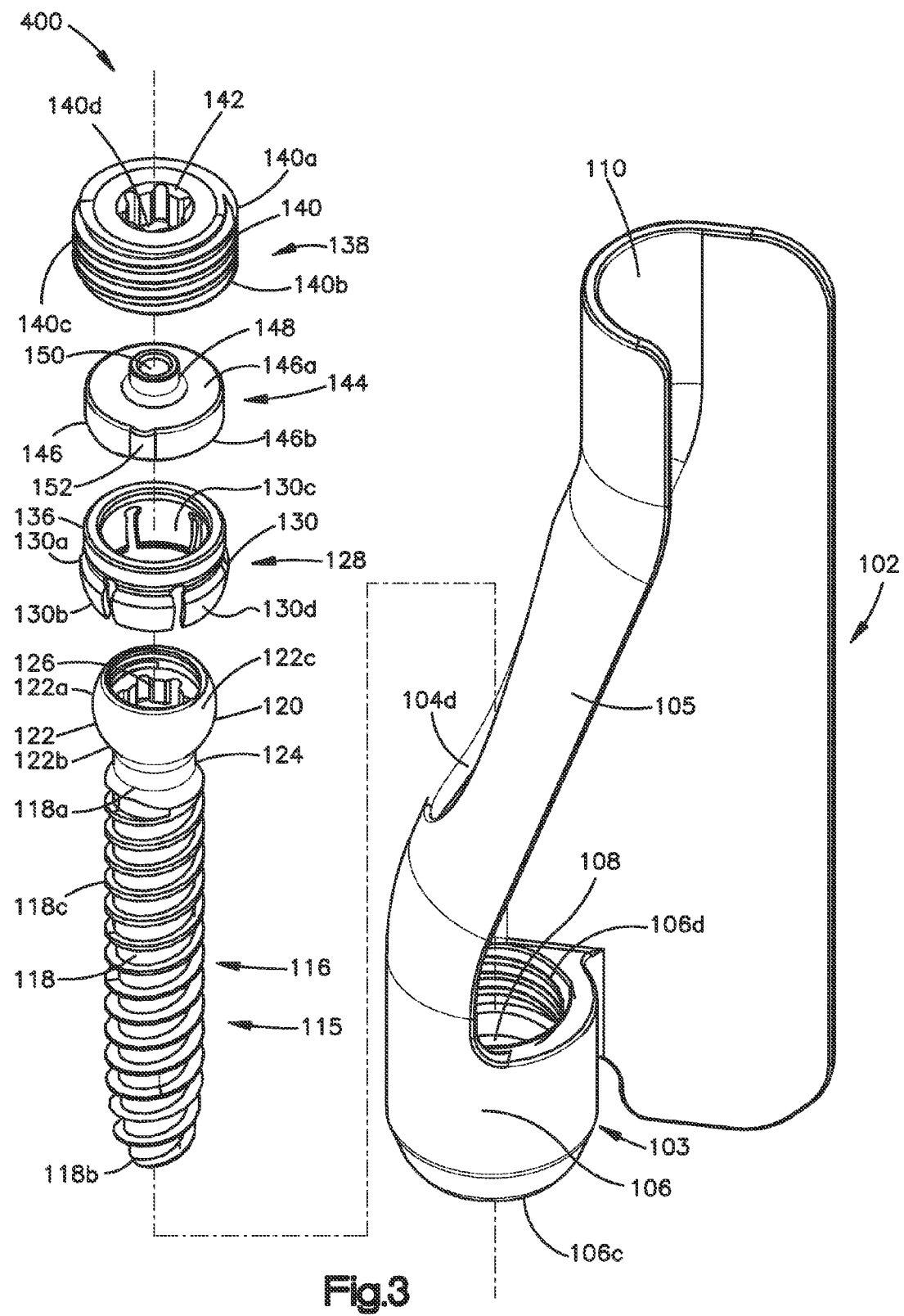
FIG. 3 is an exploded assembly view of the blade type patient-mounted retractor assembly illustrated in FIG. 1, including a retractor body, a locking cap, an intermediate wedge, a collet, and a bone anchor.

Certain terminology is used in the following description for convenience only and is not limiting. The words "right", "left", "top," "bottom," "upper," and "lower" designate directions in the drawings to which reference is made. The words "inwardly," "outwardly," "distally," and "proximally" refer to directions toward or away from the geometric center of the element being described and designated parts thereof. The words, "anterior", "posterior", "superior", "inferior", "lateral", "medial", "sagittal", "axial", "coronal," "cranial," "caudal" and related words and/or phrases designate preferred positions and orientations in the human body to which reference is made and are not meant to be limiting. The terminology intended to be non-limiting includes the above-listed words, derivatives thereof and words of similar import.

Described herein are patient-mounted retractor assemblies having varying configurations and/or features. Patient-mounted retractor assemblies may be used in surgical procedures, for example minimally invasive spinal surgeries.

Applications of patient-mounted retractor assemblies can include, but are not limited to, discectomies, laminectomies, facetectomies, pedicle screw fixation, and the like. The retractors used in the various patient-mounted retractor assemblies described herein may be configured using any geometry appropriate for retracting tissue, musculature, and other anatomical features from a surgical site, thereby facilitating access within the surgical site, for example by a surgeon performing a procedure. Patient-mounted retractors may be re-positionable within a surgical site, for example along one or more axes, thus providing additional flexibility and utility to a surgeon working within a surgical site. Unless otherwise indicated, the patient-mounted retractors, assemblies, and the various components thereof can be manufactured from any suitable biocompatible material known in the art including but not limited to titanium, titanium alloy, such as TAN, stainless steel, reinforced plastics, elastomeric materials, and the like, or any combination thereof.

The patient-mounted retractors described herein may have various features that facilitate re-configurable access to a surgical site. For example, patient-mounted retractors may have channels formed therein that themselves create, or may be used in combination with complimentary features of other retracotrs to provide, surgical site access, for example in the form of an "access portal." An access portal may comprise an exposed area within a surgical site configured such that a surgeon performing a procedure is provided with adequate visibility into a surgical site and to provide sufficient space for the deployment and/or utilization of any instrumentation required for the corresponding procedure. Example geometries described herein include "blade" type retractors, such as the retractors depicted in FIGS. 1 to 9, "tube" type, or cannulated, retractors such as the retracor depicted in FIGS. 10 to 18. However, it should be noted that these patient-mounted retractor geometries are merely examples, and the scope of the instant disclosure should not thereto. Alternative patient-mounted retractor geometries may be conceived of by those skilled in the art without straying from the spirit and scope of the instant disclosure.

Referring to FIGS. 1-3, an example embodiment of a patient-mounted retractor assembly 100 includes a blade type retractor 102, a mounting post 115 (e.g., a bone anchor 116) that can be connected to the retractor 102, and a locking assembly 400 comprising locking components such as a collet 128, an intermediate wedge 144, and a locking cap 138. As will become appreciated from the following description, the geometric characteristics of the blade type retractor 102 illustrated in FIGS. 1 to 9 provide an example of one design for a blade type patient-mounted retractor, but any alternative geometry may be used as appropriate. The blade type retractor 102 includes a retraction member in the form of a generally cylindrical retractor body 104 with a proximal end 104a, a distal end 104b opposite the proximal end, and an intermediate portion 104c defined between the proximal and distal ends 104a and 104b. It should be that the generally cylindrical geometry of the body depicted in the illustrative embodiments is merely an example body geometry, and that any other body geometries and/or body shapes for the body 104 may be used as desired. The body 104 of the retractor 102 may further include one or more accessory attachment points that may be configured to releasably receive optional accessories, such as illumination devices, suction apparatus, and the like.

The intermediate portion 104c may define an offset region 105 disposed between the proximal and distal ends 104a and 104b, respectively. For example, the proximal end 104a is centrally disposed on a first axis A1 and the distal end 104b is centrally disposed on a second axis A2 that is offset with respect to the first axis. In the example embodiment, the intermediate portion 104c is centrally disposed on an axis A3 that is offset with respect to both axes A1 and A2, thereby defining an offset region 105 of the body 104 between and with respect to the proximal end 104a and the distal end 104b. The degree of offset between the axes A1 and A2 may be tailored according to the anticipated use of the retractor, for example in accordance with a particular surgical site location within a patient, in accordance with a particular patient size and/or anatomy, and the like. It should be noted that the degree of offset between axes A1 and A2 depicted in the example embodiment illustrated in FIGS. 1-3 is merely an example offset, and the scope of the instant disclosure should not be limited thereto. For example, in an alternative embodiment, axes A1 and A2 may be coincident (i.e., there may be no offset region). In another alternative embodiment, there may be more than one, or varying degrees of offset within the offset region 105 of the intermediate portion 104c, defined along one or more additional axes. Furthermore, while the axes A1 and A2 are depicted as vertical and substantially parallel, and while axes A1, A2, and A3 are all defined within a single plane, it should be noted that axes A1 and A2 could be non-parallel with respect to each other, and/or defined within different planes in alternative embodiments, and the resulting patient-mounted retractor geometries would still be considered within the scope of the instant disclosure.

At least a portion of the body 104 of the blade type patient-mounted retractor 102 may be hollow and/or open. For instance, in the example embodiment depicted in FIGS. 1-3, the body 104 of the blade type retractor 102 is closed at the distal end 104b, hollow and open in the intermediate portion 104c, throughout the offset region 105, and hollow and open at the proximal end 104a, defining a curved plate 111 with opposing lateral edges 117. In alternative embodiments, the body 104 of the retractor 102 may be solid between the proximal and distal ends 104a and 104b, respectively, may be solid and/or closed at the proximal end 104a, may be solid and/or closed at the distal end 104b, or any combination thereof.

The body 104 of the blade type patient-mounted retractor 102 may include an auxiliary retraction member in the form of a flange 112 including a flange body 113 that defines a proximal end 113a, a distal end 113b opposite the proximal end 113a, and a lateral edge 113c. In the example embodiment, the flange 112 extends outwardly from one of the lateral edges 117 between the proximal and distal ends 104a and 104b of the body 104. The flange 112 may extend outwardly from the body 104 in any direction as appropriate. For example, the flange 112 may extend tangentially from an outer perimeter of the body 104, may extend outwardly along a chord defined between two points on a circumference of the body 104, or in any other direction as appropriate. In the illustrative embodiment, the lateral edge 113c has a vertical profile that is essentially parallel with axes A1 and A2. In alternative embodiments, the lateral edge may be defined along an axis offset with respect to axes A1, A2, and/or A3, may have one or more sections of curvature, may have cutouts therefrom, or any combination thereof.

The vertical contour of the flange 112, as defined by the plane of the flange 112, can conform to the shape of the body 104 between the proximal and distal ends 104a and 104b, or may be defined independently of the geometry of the body. In the example embodiment illustrated in FIGS. 1 to 3, the vertical contour of the flange 112 is essentially coplanar with the lateral edge 117 from which it extends. However, it should be noted the geometry of the flange 112 depicted in FIGS. 1 to 3 is merely an example, and the scope of the instant disclosure should not be limited thereto. For instance, the flange body 113 of the flange 112 can exhibit one or more sections having bends and/or areas of curvature formed along one or more axes and/or within one or more planes with respect to the body 104, areas of concavity and/or convexity, or any combination thereof. The geometry of the flange 112 may be determined in part in accordance with a particular surgical site location within a patient, in accordance with a particular patient size and/or anatomy, and the like. In alternative embodiments, the body 104 of the blade type patient-mounted retractor 102 may define more than one flange 112 (not shown). In such embodiments, the flanges 112 may be configured with similar or disparate geometries, vertical contours, etc., with respect to each other.

The flange 112 may have one or more tabs 114 extending from the flange body 113, and in particular extending distally from the distal end 113b of the flange body 113. The tab 114 may be configured to aide in the retraction of flesh, musculature, and the like when the blade type retractor is positioned and mounted in a surgical site. For example, the tab 114 may be configured to flexibly conform to bony anatomy when the retractor 102 is inserted into a surgical site, and in conforming to the bony anatomy may perform a scooping action to retract material located in close proximity to the bony surface that might otherwise obstruct visibility into the surgical site. If more than one tab 114 is desired, a series of slots (not shown) may be formed within the tab 114 and/or the distal end 113b of the flange body 113, thereby defining a plurality of tabs. If the material properties of the retractor body 104 and/or the flange 112 do not exhibit a desired level of flexibility, one or more sections of flexible skirting made of a suitably elastomeric material, may be affixed to the distal end 113b of the flange body 113 in lieu of the tab 114. The shape and geometry of the tab 114 with respect to the flange 112 may be configured as appropriate, for example in accordance with a particular patient size and/or anatomy, and the like.

Figure 8:
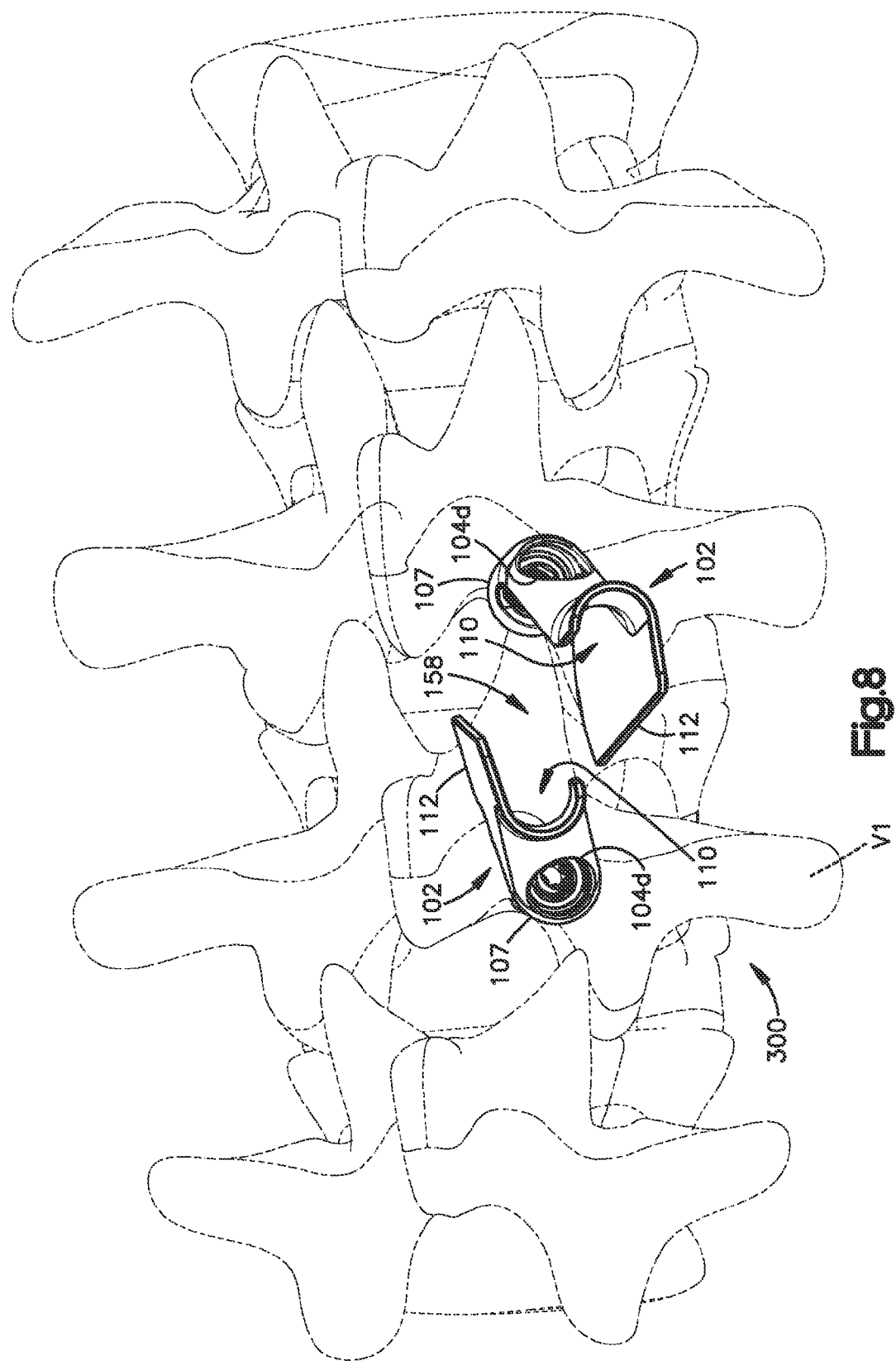
FIG. 8 is a perspective view of a retractor system including two blade type patient-mounted retractor assemblies disposed in a surgical site in accordance with an embodiment.
Figure 9:
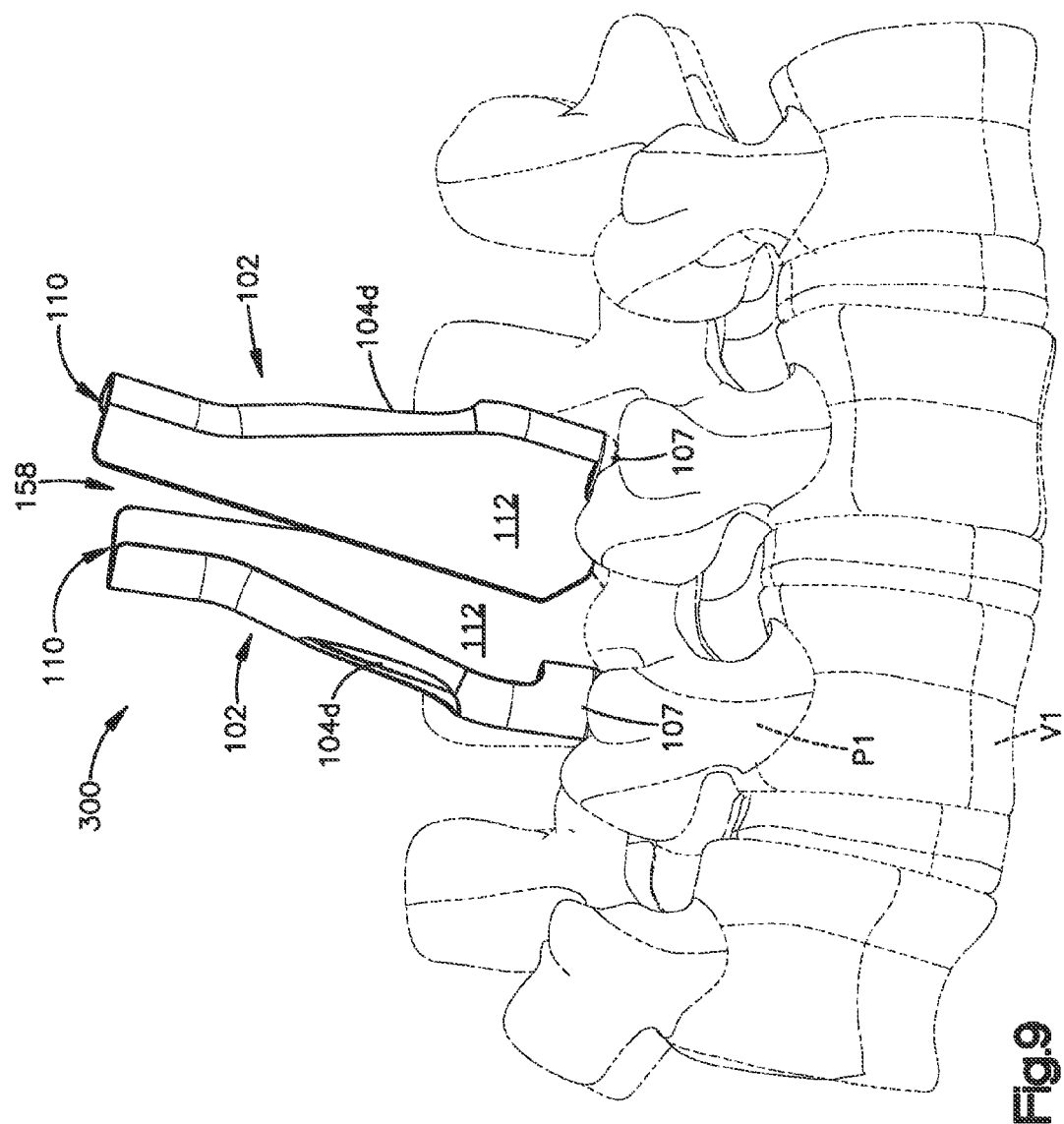
FIG. 9 is another perspective view of the retractor system illustrated in FIG. 8.
Figure 10:
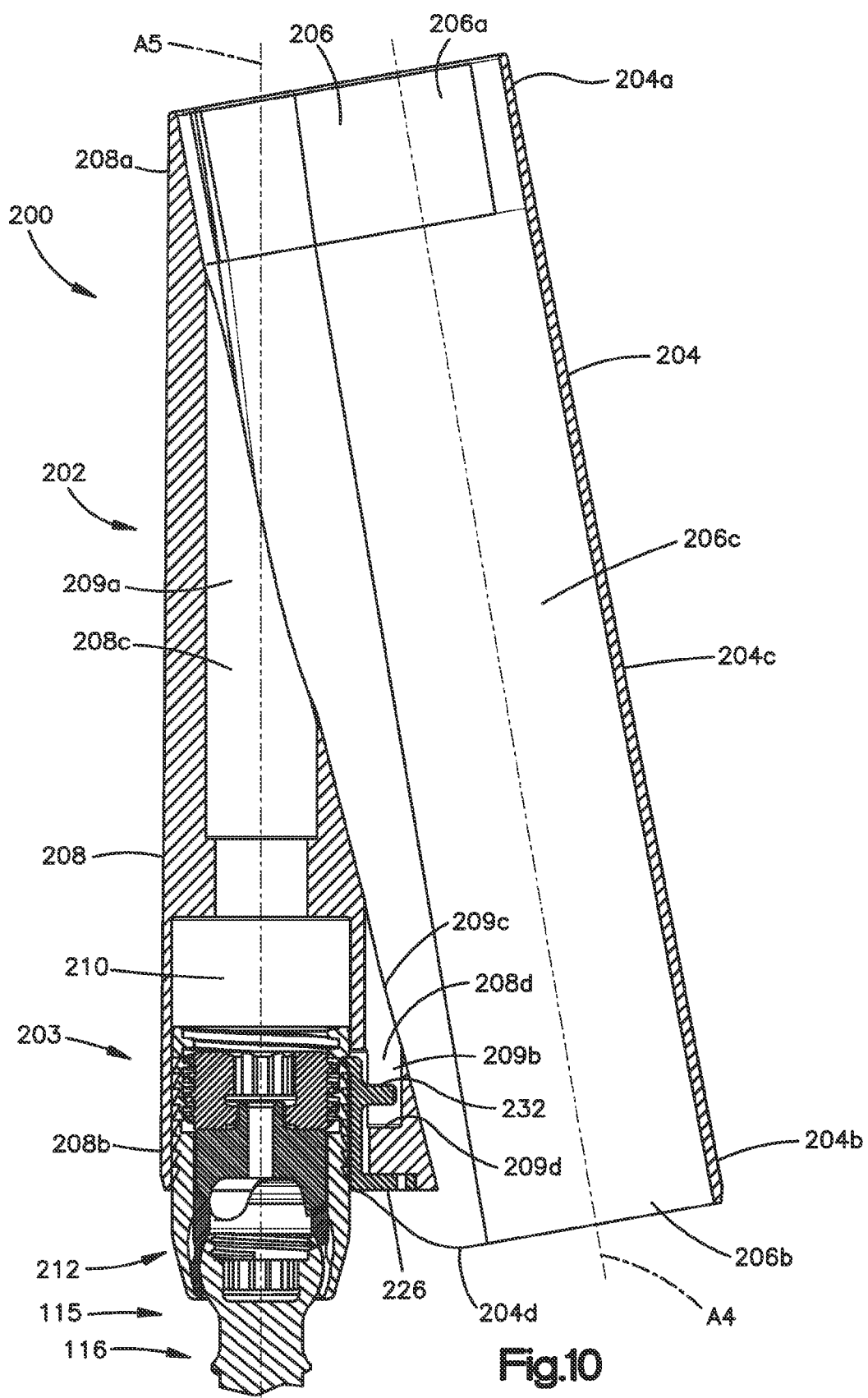
FIG. 10 is a cross sectional view of a tube type patient-mounted retractor assembly in accordance with an embodiment.

The body 104 of the blade type patient-mounted retractor 102 may define a channel 110. The channel 110 may be configured to provide access to a surgical site when the patient-mounted retractor is mounted to a patient. The channel 110 may be defined by the body 104, alone or in combination with additional retraction members of the retractor, such as the flange 112. In this regard, it can be said that the channel 110 is at least partially defined by the body 104. The channel 110 may define any suitable shape, geometry, length, etc. as desired. For instance, in the example embodiment illustrated in FIGS. 1-3, the channel 110 is defined longitudinally by the hollow portions of the body 104 between the opening at the proximal end 104a of the body and the closed distal end 104b, and outwardly along the surface of the flange 112. The channel 110 may be configured to provide visibility and instrument access to a surgical site when mounted to a patient, thereby creating an access portal 158 in the surgical site. A retractor system 300, including two or more blade type patient-mounted retractor assemblies 100, may be used to create access portals 158 of varying sizes and/or geometries, as depicted in FIGS. 8 and 9 and discussed in greater detail below.

The blade type patient-mounted retractor 102 may be mounted to a patient by connecting the body 104 of the retractor to a mounting post 115. The mounting post 115 may be any type of fastener suitable to be removably inserted into a patient at a surgical site, for example a bone anchor, a nail, a pedicle mounting post, and the like. In the example embodiment depicted in FIGS. 1 to 9, the mounting post 115 is a bone anchor 116. In preferred embodiments, the blade type retractor 102 and the mounting post 115 are configured to allow the retractor to be polyaxially rotated or positionable about the mounting post 115 when the retractor 102 is connected to the mounting post 115. Rotation of the retractor about the mounting post 115 can allow a surgeon to initially position, and subsequently reposition if necessary, the retractor 102 as needed in order to maximize its utility in the surgical site. In alternative embodiments, the retractor body 104 and the mounting post 115 may be rigidly fixed with respect to one another prior to insertion of the retractor 102 in a surgical site.

The retractor assembly 100 can further include a mounting member 103 that can connect the body 104 of the blade type patient-mounted retractor 102 to the bone anchor 116. The mounting member 103 can be affixed to and/or formed in the body 104. In the example embodiment illustrated in FIGS. 1 to 3, the mounting member 103 is an anchor receptacle 106. The anchor receptacle 106 includes a proximal end 106a, and a distal end 106b opposite the proximal end. The anchor receptacle 106 may be formed within the body 104, or otherwise affixed to the body 104. In the example embodiment depicted in FIGS. 1 to 3, the anchor receptacle 106 is defined by the distal end 104b of the body 104. The anchor receptacle 106 may be configured in accordance with the type of mounting post 115 to which the blade type retractor 102 will connect. For example, the anchor receptacle 106 may define an aperture 108 therein, the aperture 108 configured to receive the head of the bone anchor 116. In alternative embodiments, the anchor receptacle 106 may have a bore (such as the bore 210 illustrated in FIG. 10) formed within the distal end 106b, the bore configured to receive the anchor cartridge 212 discussed in more detail below with reference to the tube type patient-mounted retractor 202. Additional components of the retractor assembly 100 may also be disposed within the aperture 108 of the anchor receptacle, for example the components of the locking assembly 400.

In the example embodiment depicted in FIGS. 1-3, the distal end 106b of the anchor receptacle 106 can be open and tapered or otherwise narrowed with respect to the proximal end 106a, so as to define a socket 106c at the distal end 106b. The socket 106c can be configured to retain a collet 128 as described in more detail below. Alternatively, the socket 106c may be configured to retain a head 120 of the bone anchor 116. It should be noted that the anchor receptacle 106 can be disposed at the distal end 104b of the body 104 merely as an example anchor receptacle location, and that the anchor receptacle 106 could be formed in and/or affixed to any other location on the body 104 as desired.

The bone anchor 116 includes a shaft 118 that defines longitudinally opposing proximal and distal ends 118a and 118b respectively, and a head 120 coupled to the proximal end 118a of the shaft 118. Helical threads 118c extend circumferentially around the shaft 118 along a substantial entirety of the shaft between the proximal and distal ends 118a and 118b, respectively. The helical threads 118c are configured to engage underlying bone. In one embodiment, the threads 118c may define an outer diameter that remains substantially constant between the proximal and distal ends. In alternative embodiments, the outer diameter defined by the threads 118c may vary over the length of the shaft, such that the outer diameter at the proximal end 118a is greater in magnitude than the outer diameter of the threads at the distal end 118b, or such that the outer diameter at the proximal end 118a is lesser in magnitude than the outer diameter of the threads at the distal end 118b. The shaft 118 of the bone anchor 116 may be cannulated, such that the bone anchor 116 may receive a guide wire in order to direct the trajectory of the bone anchor 116 when it is driven into position within a patient.

The head 120 includes an annular body 122 that defines a proximal end 122a, a distal end 122b opposite the proximal end, and a curved outer surface 122c. The annular body 122 may be defined in the shape of a segment of a sphere having a diameter or cross-sectional dimension that is greater at a location between the proximal and distal ends than at either of the proximal and distal ends 122a and 122b respectively. Defining the annular body 122 in the shape of a segment of a sphere allows polyaxial rotation about the head 120 of the bone anchor 116. It should be noted that the head 120 can assume any other suitable shape as desired. The distal end 122b of the head is formed and/or coupled to the proximal end 118a of the shaft, either directly or indirectly via neck 124. The head may have driving features 126 formed therein, for example at the proximal end 122a, the driving features configured to engage with complimentary driving features of a driving instrument (not shown).

As mentioned above, in preferred embodiments, the retractor 102 can be polyaxially positionable about the mounting post 115 when the retractor 102 is connected to the mounting post 115. The retractor assembly 100 can include a locking assembly 400 that can be connected to the retractor body 104, for example disposed within the anchor receptacle 106. The locking assembly 400 can include a collet 128, a locking cap 138, and an intermediate wedge 144. When the blade type retractor 102 has been connected to a mounting post 115, for example bone anchor 116, and positioned as desired within the surgical site, the retractor body 104 can be positionally fixed with respect to the mounting post 115 by engaging the locking assembly 400 to a locked configuration.

The collet 128 includes an annular body 130 that defines a proximal end 130a, a distal end 130b opposite the proximal end, a concave inner surface 130c, and an opposing convex outer surface 130d. The annular body 130 can define the shape of a segment of a sphere, having a diameter or cross-sectional dimension that is greater at a location between the proximal and distal ends than at either of the proximal and distal ends 130a and 130b.

The concave inner surface 130c may define a spherical shape that substantially matches the curved outer surface 122c of the head 120 of the bone anchor 116, such that the concave inner surface 130c will be engaged with the curved outer surface 122c when the head 120 of the bone anchor 116 is received in the collet 128. The inner surface of the socket 106c may be configured in the shape of a segment of a sphere with a spherical volume that is substantially the same as or slightly greater in magnitude than the spherical volume of the convex outside surface 130d of the collet 128. The annular body 130 further includes a plurality of circumferentially spaced retention fingers 132 formed within the distal end 130b of the annular body 130. The retention fingers 132 are configured such that circumferentially adjacent fingers 132 are separated by a slot 134 that extends proximally upwards into the body 130 from the distal end 130b.

The retention fingers 132 are configured to retain the head 120 of the bone anchor 116. As the collet 128 is first disposed onto the head 120 of the bone anchor 116, the retention fingers 132 deflect, spreading outwardly from the center of the collet along the curved outer surface 122c of the head 120. Once the tips at the distal ends of the fingers 132 move beyond the portion of the curved outer 122c surface with the largest diameter between the proximal and distal ends 122a and 122b, the fingers 132 "snap" back to their original shape, thus releasably retaining the head 120 of the bone anchor within the collet 128 via a snap fit. The spherical inner surface of the socket 106c is sufficiently sized to accommodate snapping the collet 128 into place over the head 120 of the bone anchor 116, and for removal of the bone anchor from the collet, while the collet and the bone anchor are disposed within the anchor receptacle 106.

The collet 128 may be retained in the aperture 108 of the anchor receptacle by a locking cap 138 and an intermediate wedge 144. The collet 128 includes an annular ring 136 formed at the proximal end 130a of the annular body 130. The annular ring 136 is configured to engage the lower surface 146b of the intermediate wedge 144 or the bottom surface of a locking cap 138, and to provide axial alignment of the collet within the aperture 108 of the anchor receptacle 106. The locking cap 138 includes a body 140 defining a proximal end 140a, a distal end 140b opposite the proximal end. Helical threads 140c, configured to engage complimentary threads 106d formed within the surface of the aperture 108 at the proximal end 106a of the anchor receptacle 106, extend circumferentially around the body 140 along a substantial entirety of the body between the proximal and distal ends. The locking cap 138 may have driving features 142 formed therein, for example at the proximal end 140a. The driving features 142 are configured to engage with complimentary driving features of a driving instrument (not shown). The locking cap 138 may have a longitudinal aperture 140d formed therethrough. The aperture 140d is configured to receive a raised collar 148 of the intermediate wedge 144. The locking cap 138 may be configured to be removable from the anchor receptacle 106, or alternatively may be configured to be captive within the anchor receptacle 106, and therefore non-removable.

The intermediate wedge 144 may be disposed within the aperture 108 of the anchor receptacle 106, at a location between the collet 128 and the locking cap 138. The intermediate wedge 144 includes a generally cylindrical shaped body 146 defining an upper surface 146a at the proximal end of the body and an opposing lower surface 146b at the distal end of the body. The body 146 further includes a raised collar 148 extending upwardly from the upper surface 146a at the proximal end of the body 146, the collar configured to be received within the longitudinal aperture 140d of the locking cap 138. A longitudinal aperture 150 may extend through the raised collar 148 and the body 146. The aperture 150 can have a diameter that is sufficiently large to allow a guide wire to pass through. The intermediate wedge 144 may have one or more raised ridges 152 formed on the outer surface of the body 146 between the proximal and distal ends 146a and 146b. The raised ridge 152 may be configured to slidably engage with a complimentary slot (not shown) formed in the surface of the aperture 108 of the anchor receptacle 106. The raised ridge 152, when received in slidable engagement with the complimentary slot in the anchor receptacle 106, prevents rotation of the intermediate wedge 144 within the aperture 108.

Figure 6:
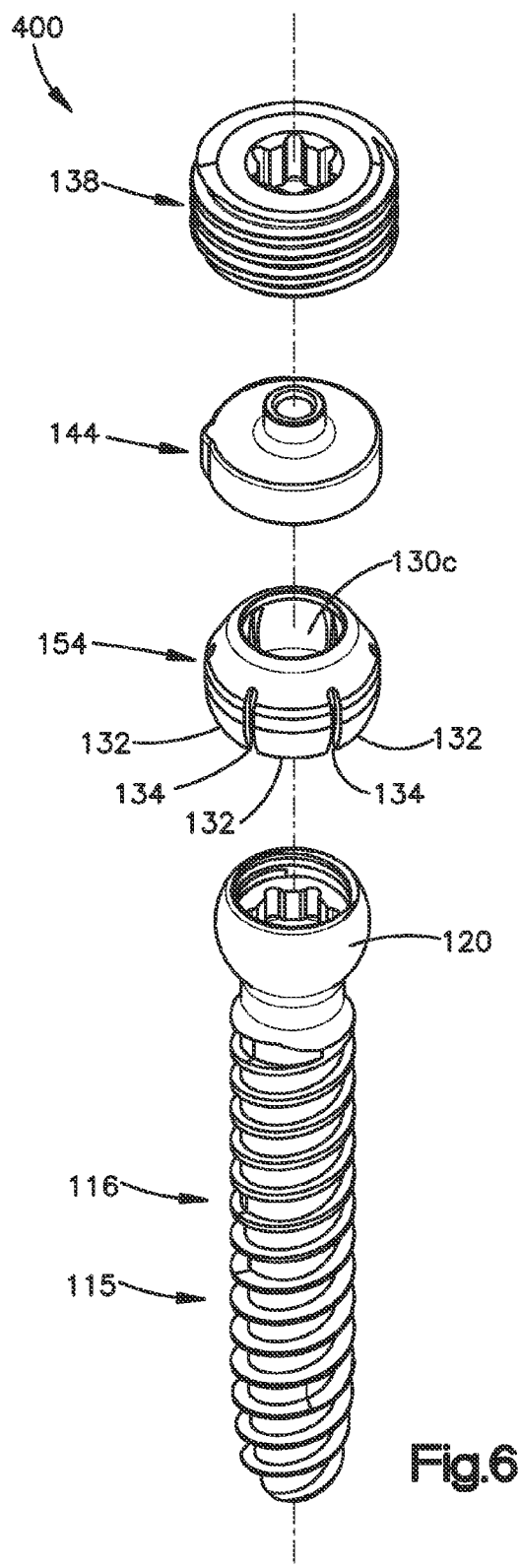
FIG. 6 is an exploded assembly view of the blade type patient-mounted retractor assembly similar to FIG. 3, but constructed in accordance with an alternative embodiment.
Figure 7:
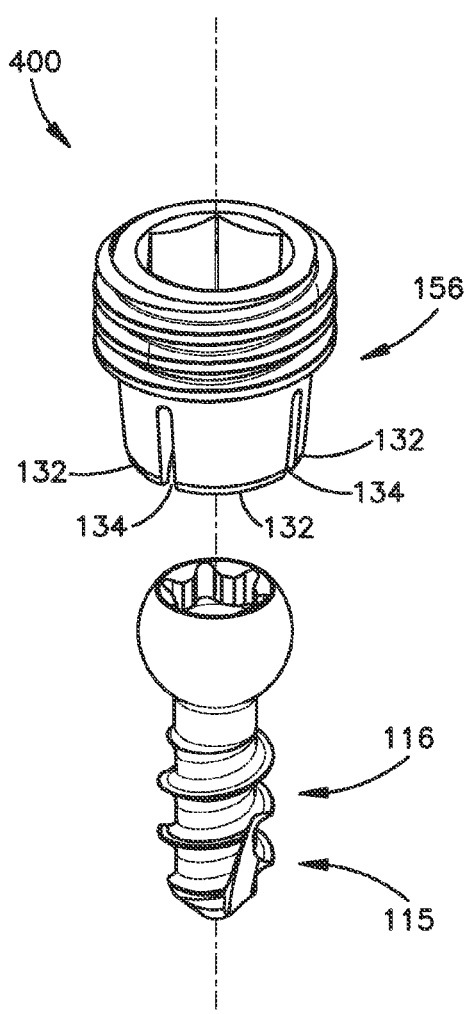
FIG. 7 is an exploded assembly view of a blade type patient-mounted retractor assembly constructed in accordance with an alternative embodiment, including a collet with an integrated locking cap.

The lower surface 146b of the body 146 may be configured as a relatively flat plane configured to engage with the annular ring 136 of collet 128. In accordance with an alternative embodiment, a collet 154 (as depicted in FIG. 6) replaces the collet 128 in the locking assembly 400, and the intermediate wedge 144 may be configured accordingly with a substantially concave lower surface 146b configured to engage with the spherical upper surface of the collet 154, thereby providing an enhanced magnitude of surface area contact between the collet 154 and the intermediate wedge 144 with respect to the magnitude of surface area contact between the collet 128 and the intermediate wedge 144. Enhancing the magnitude of surface area contact between a collet and an intermediate wedge can result in a more robust interface between the locking components of the locking assembly 400 when the locking assembly 400 is activated to a locked configuration.

In an example method of using the blade type patient-mounted retractor 102, a mounting post 115, for example the bone anchor 116, is inserted into an underlying target location 107 of a patient at a surgical site. The target location 107 can be an underlying bone such as a vertebral body V1. In accordance with one embodiment, the target location 107 is a pedicle P1 of the vertebral body V1. The blade type retractor 102 may then be connected to the head of the bone anchor 116. The blade type retractor 102 may have the anchor receptacle 106 disposed at the distal end 104b of the retractor. The anchor receptacle may have locking components disposed within it, for example a collet (e.g., collets 128 or 154), an intermediate wedge 144, and a locking cap 138. It should be noted that certain of these locking components of the locking assembly 400 may be omitted, as discussed in more detail below. To aide deployment of the blade type patient-mounted retractor, it may be desirable to first locate a desired insertion point for the bone anchor via the insertion of a guide wire. A cannulated version of the bone anchor 116 may then be inserted into the surgical site over the guide wire to guide the trajectory of the bone anchor 116 as it is driven into the desired surgical location. The guide wire may also be passed through the anchor receptacle 106 and the locking assembly 400 disposed therein, and used to guide the alignment of the collet with the head of the bone anchor.

The retractor 102 may be connected to the bone anchor 116 by snapping the collet 128 that is disposed in the anchor receptacle 106 over the head 120 of the bone anchor 116. When the retractor body 104 is connected to the head 120 of the bone anchor 116, the retractor 102 can be rotatably positionable about the head 120 of the bone anchor 116. Once the blade type retractor 102 has been positioned to provide the desired access portal 158 at the surgical site, the retractor body 104 may be fixed with respect to the bone anchor 116 by activating the locking assembly 400 to the locked configuration. Although a single blade type retractor 102 can be used to define an access portal 158, greater flexibility is achieved when two or more blade type retractors are deployed at a surgical site, as depicted in FIGS. 8 and 9. In FIGS. 8 and 9, a retractor system 300 including two blade type retractor assemblies 100 is mounted to respective target locations 107 that are spaced from each other at a surgical site, such that the respective retractors 102 oppose each other. In particular, the retractors 102 are positioned such that the respective channels 110 face each other so as to form the access portal 158 at the surgical site. The access portal 158 is re-configurable, for example during the course of a procedure, by releasing the locking assembly 400 of one or both of the retractor assemblies 100 to an unlocked configuration, repositioning one or both of the retractors 102 to reconfigure the access portal 158 as desired, then re-activating the locking assembly 400 of the respective retractor assembly 100 or assemblies 100 to the locked configuration, thereby securing the respective retractor 102 or retractors 102 in their new positions.

In one example of activating the locking assembly 400 of a blade type patient-mounted retractor 102, for example using the collet 128 or 154, the intermediate wedge 144, and the locking cap 138, a driving instrument may be inserted into the channel 110 of the corresponding retractor 102, and a rotational driving force applied to the locking cap 138, thereby advancing the locking cap 138 in a distal, or downward, direction within the anchor receptacle 106, toward the collet 128. If access to the channel 110 would be blocked by the geometry of the body 104 of the retractor 102, an instrument aperture 104d may be formed within the body 104. The aperture 104d can be configured to allow access by a driving instrument to the anchor receptacle 106. If an intermediate wedge 144 is disposed between the locking cap 138 and the collet 128, the advancing locking cap 138 will transfer downward force to the intermediate wedge 144, causing the intermediate wedge 144 to advance in a distal or downward direction within the anchor receptacle 106. As the intermediate wedge 144 advances, the lower surface 146b of the wedge 144 makes contact with the proximal end of the collet 128, thereby transferring downward force to the collet 128 and causing the retention fingers 132 to interfere with the inner surface of the socket 106c at the distal end 106b of the anchor receptacle 106, and to collapse around the head 120 of the bone anchor 116, thereby fixing the anchor receptacle 106, and thus the retractor body 104, in position with respect to the head 120 of the bone anchor 116 via a crush lock between the collet 128 and the bone anchor 116.

If a surgeon performing a procedure desires to reposition the blade type patient-mounted retractor 102, a rotational driving force of the opposite direction to that applied during activation of the locking assembly 400 may be applied to release the locking assembly 400 to its unlocked configuration, thereby re-enabling polyaxial positioning of the retractor 102 with respect to the bone anchor 116. When the retractor 102 is repositioned as desired, the locking assembly 400 can be activated again to its locked configuration as described above to re-lock the retractor 102 in position with respect to the head 120 of the bone anchor 116. The blade type patient-mounted retractor 102 can be removed from the surgical site by releasing the locking assembly 400 and applying an upward force to the retractor body 104, thereby causing the collet 128 to disengage from the head 120 of the bone anchor 116. The bone anchor 116 may be removed from the surgical site, or may be re-used, for example as a bone anchoring element of a bottom-loading pedicle screw assembly. It should be noted that while the instant example method is discussed within reference to the use of solely blade type patient-mounted retractors, it is possible to use blade type patient-mounted retractors in conjunction with tube type patient-mounted retractors during a single procedure.

As described above, various embodiments of the locking assembly 400 may omit one or more of the locking components described above. For example, it is possible to omit the intermediate wedge 144 in certain embodiments. When the intermediate wedge 144 is omitted, the lower surface of the locking cap 138 makes direct contact with the collet 128 as the locking cap 138 is advanced in the anchor receptacle 106. In embodiments where the intermediate wedge 144 is so omitted, the upper surface of the collet 128 at the proximal end 130a may have an engagement structure formed thereon, the engagement structure configured to engage the lower surface of the locking cap 138 as it is advanced, thereby transferring downward force from the locking cap 138 to the collet 128. The lower surface of the locking cap 138 may similarly include engagement structure formed thereon, the engagement structure configured to engage the upper surface of the collet 128 as the locking cap 138 is advanced. Alternatively, both the lower surface of the locking cap 138 and the upper surface of the collet 128 may have complimentary engagement structure formed thereon. In accordance with another alternative embodiment of the locking assembly 400, the locking cap 138 and the collet 128 can be combined into a unitary locking collet 156, depicted in FIG. 7.

It should be noted that although locking the retractor body 104 in position with respect to the bone anchor 116 has been discussed with reference to the locking assembly 400 disposed within the anchor receptacle 106, the scope of the instant disclosure should not be limited thereto. For instance, the retractor body 104 may alternatively be connected to the bone anchor 116 and/or locked in place with respect to the bone anchor 116 via alternatively constructed locking assemblies. For example, the curved outer surface 122c of the head 120 of the bone anchor 116 may have helical threads formed thereon, the threads configured to engage complimentary threads formed within the distal end 106b of the anchor receptacle 106. Alternatively, the head 120 of the bone anchor 116 and the anchor receptacle 106 may have ball and detent features disposed therein, thereby providing predetermined angulation settings between the retractor body and the bone anchor and toolless adjustment. Of course any other components and/or mechanisms can be used to connect the blade type retractor to the bone anchor and/or lock the position of the retractor in position with respect to the bone anchor as desired.

Now referring to FIGS. 10-18, a patient-mounted retractor assembly 200 can be constructed in accordance with an embodiment. The retractor assembly 200 can include a tube type retractor 202, a mounting post 115, a locking assembly 500 configured to secure the mounting post 115 to the retractor 202, and an anchor cartridge 212 that is configured to provide axial translation of the retractor 202 with respect to the mounting post 115, and can carry components of the locking assembly 500. As will become appreciated from the following description, the body geometry characteristics of the tube type retractor 202 illustrated in FIGS. 10-18 provide an example of one design for a tube type patient-mounted retractor, but alternative body geometries may be used as appropriate. The tube type retractor 202 includes a generally tube shaped retractor body 204 defining a proximal end 204a, a distal end 204b opposite the proximal end, and an intermediate portion 204c disposed between the proximal end 204a and the distal end 204b. The retractor 202 further includes at least one bore 206 formed through the body 204 along a longitudinal axis A4. The bore 206 defines a first opening 206a at the proximal end 204a of the body 204, a second opening 206b disposed at the distal end 204b of the body 204, and an intermediate section 206c between the first opening 206a and the second opening 206b. The bore 206 may serve of similar use as the channel 110 and/or access portal 158 defined by the blade-type patient-mounted retractor 102, in that the bore 206 may provide visibility into a surgical site and space for the deployment and/or utilization of instrumentation to be used during a surgical procedure. In alternative embodiments, two or more bores 206 may be formed within the body 204 of the tube type retractor. The body 204 of the retractor 202 may further include one or more accessory attachment points that may be configured to releasably receive optional accessories, such as illumination devices, suction apparatus, and the like.

A cross sectional dimension of the bore can vary between the proximal and distal ends 206a and 206b, respectively. For example, the cross sectional dimension may be the diameter of the bore 206. In the illustrative environment, the first opening 206a has a diameter of greater magnitude than the diameter of the second opening 206b. The diameter of the bore 206 gradually decreases along the intermediate section 206c from the first opening 206a to the second opening 206b. In an alternative embodiment the first opening 206a may have a diameter of lesser magnitude than the diameter of the second opening 206b, and the diameter of the bore 206 may gradually increase along the intermediate section 206c from the first opening to the second opening. In another embodiment, the first and second openings 206a and 206b may have diameters of equal magnitude, and the diameter of the bore 206 may remain constant along the intermediate section 206c. In another alternative embodiment, the diameter may vary along the intermediate section 206c, regardless of the diameter of the first opening 206a or the second opening 206b. Of course other cross sectional dimensions, such as area, may be used to define the characteristics of the bore 206.

The distal end 204b of the body 204 may have a profiled edge 204d formed therein at a location proximate to the second opening 206b. The geometry of the profiled edge 204d may be defined at least in part in accordance with the intended use of the tube type retractor, for example in accordance with the underlying bony anatomy that the distal end 204b of the retractor may engage in a surgical site. For example, the profiled edge 204d can include one or more angled and/or curved cutout sections defined along the perimeter of the distal end 204d of the body, the cutout sections configured to conform to bony structure or other patient anatomy at a surgical site.

The retractor 202 can include one or more tabs 214 extending distally from the distal end 204b of the body 204, for example along the profiled edge 204d, as illustrated in FIG. 11. The tabs 214 may be configured to aide in the retraction of flesh, musculature, and the like when the tube type retractor is positioned and mounted in a surgical site. For example, the tabs 214 may be configured to flexibly conform to bony anatomy when the retractor 202 is inserted into a surgical site, and in conforming to the bony anatomy may perform a scooping action to retract material located in close proximity to the bony surface that might otherwise obstruct visibility into the surgical site. The tabs 214 may be separated by a series of slots 216 extending from the distal end 204b of the body 204 upward towards the proximal end 204a. The number and length of the slots 216 may determine the flexibility, and thus the conforming characteristics, of the tabs 214. If the material properties of the retractor body 204 do not exhibit a desired level of flexibility, one or more sections of flexible skirting 218, made of a suitably elastomeric material, may be affixed to the distal end 204b of body in lieu of the tabs 214, as illustrated in FIG. 12.

The tube type patient-mounted retractor 202 includes a generally circular bore 206 that extends through the body 204, and a straight intermediate section 204c extending between the proximal and distal ends 204a and 204b of the body 204. It should be appreciated, however, that the shape of the bore 206 and the body 204 are merely example shapes, and the scope of the instant disclosure should not be limited thereto. Tube type patient-mounted retractors 202 with many variations of the above shapes are possible and are intended to be included within the scope of the instant disclosure. For example: the geometry of the bore 206 may be elliptical, square, rectangular, hexagonal, or any other shape; the geometry of the retractor body 204 may conform to the geometry of the bore, or the body 204 may have a different geometry from the bore (e.g., a circular bore through a square body); and the intermediate section 206c of the bore 206 may have one or more areas of bends, steps, curvature, differing geometry, or other variations from straightness and/or uniformity of geometry. The geometric characteristics of the tube type retractor 202 may be determined in accordance with, for example, with a particular surgical site location within a patient, in accordance with a particular patient size and/or anatomy, and the like.

The retractor assembly 200 can include a mounting post 115 configured to connect to the tube type patient-mounted retractor 202, and in particular to the retractor body 204. The mounting post 115 may be inserted into a target location 109 of the patient at a surgical site so as to, in turn, mount the retractor 202 to the patient. The mounting post 115 may be provided as any type of fastener suitable to be removably inserted into a patient at a surgical site, for example a bone anchor, a nail, a pedicle mounting post, and the like. In accordance with the illustrated embodiment, the mounting post 115 is the bone anchor 116. In preferred embodiments, the tube type retractor 202 and the mounting post 115 are configured to allow the retractor 202 to be rotatable or polyaxially positionable about the mounting post 115 when the retractor 202 is connected to the mounting post 115. The rotatability of the retractor 202 to the mounting post 115 allows a surgeon to initially position, and subsequently reposition if necessary, the retractor 202 as needed in order to maximize its utility in the surgical site. In alternative embodiments, the retractor 202 and the mounting post 115 may be rigidly fixed with respect to one another prior to insertion in a surgical site.

The body 204 of the tube type patient-mounted retractor 202 can be connected to the bone anchor 116 utilizing a mounting member 203 affixed to and/or formed in the body 204. In accordance with the illustrated embodiment, the mounting member 203 is an anchor receptacle 208. The anchor receptacle 208 can be formed on the body 204 of the retractor 202 between the proximal and distal ends 204a and 204b, respectively, and adjacent to the bore 206. The anchor receptacle 208 includes a proximal end 208a, and a distal end 208b opposite the proximal end 208a. A cylindrical bore 210 is formed in the distal end 208b of the anchor receptacle 208. The bore 210 is configured to receive an anchor cartridge 212 discussed in more detail below. In alternative embodiments, the anchor receptacle 208 may have an aperture and/or a socket formed therein as described above with respect to the aperture 108 and socket 106c formed in the anchor receptacle 106 of the blade type patient-mounted retractor 102. A locking assembly constructed as described above with respect to the locking assembly 400 of the blade type patient-mounted retractor 102 may be disposed in such an aperture.

The anchor receptacle 208 may be formed within the body 204, or otherwise affixed to the body. In accordance with the illustrated embodiment, the anchor receptacle 208 is formed at the distal end 204b of the body 204, at a location adjacent to the bore 206. The cylindrical bore 210 is formed in the anchor receptacle 208 along an axis AS that is offset from the longitudinal axis A4. The degree of offset between the axes A4 and AS may be determined by the desired resulting geometry of the tube type retractor, for example in accordance with a particular surgical site location within a patient, in accordance with a particular patient size and/or anatomy, and the like. In order to provide access, for example by a driving instrument, to structures used in configuring and/or reconfiguring the position of the tube type retractor 202 in a surgical site, access channels 208c and 208d may be formed within the anchor receptacle 208. More or fewer access channels may be formed as necessary. Access channel 208c can be defined by a longitudinal bore 209a that extends distally along axis A5 from the first opening 206a of the bore 206 and into the bore 210. Access channel 208d can be defined by a longitudinal bore 209b that extends between a bore opening 209c, defined within the intermediate section 206c of the bore 206 above an engagement member, and a distal end 209d located below the engagement member. It should be noted that while the anchor receptacle 208 is disposed adjacent to the bore 206 at the distal end 204b of the body 204 in accordance with the illustrated embodiment, the anchor receptacle 208 can alternatively be formed in and/or affixed to any other location on the body 204 as desired.

The anchor cartridge 212 is configured to be received in the bore 210 of the anchor receptacle 208. The anchor cartridge 212 includes a cartridge body 220 defining a proximal end 220a, a distal end 220b opposite the proximal end, and an outside surface 220c. The anchor cartridge 212 can define an aperture 222 that extends through the body 220. Locking components of the locking assembly 500 or the locking assembly 400 can be disposed in the aperture 222 of the anchor cartridge 212. Helical threads 220e, configured to engage complimentary threads 140c of the locking cap 138, may be formed within the surface of the aperture 222 at the proximal end 220a of the anchor cartridge 212. The distal end 220b of the anchor cartridge 212 may be open and tapered or otherwise narrowed with respect to the proximal end 220a, thereby defining a socket 220d. In one embodiment, the socket 220d is configured to retain a collet 232. Alternatively, the socket 220d may be configured to retain the head 120 of the bone anchor 116.

The anchor cartridge 212 is configured to be axially translated within the bore 210 of the anchor receptacle 208. In a preferred embodiment, the outer surface 220c of the anchor cartridge 212 has a series of annular ridges 224 formed thereon. The annular ridges 224 are configured to be engaged by an engagement member disposed within the bore 210 of the anchor receptacle 208, such as the pawl 226. The pawl 226 includes a base 228. The base can be configured to be received within the aperture 229 formed in the distal end 208b of the anchor receptacle 208. The base 228 can be affixed to the anchor receptacle 208, for example by a fastener inserted through bore 228a and received in the distal end 208b of the anchor receptacle. The pawl 226 further includes an arm 230 defining a proximal end 230a, a distal end 230b opposite the proximal end 230a, and an engagement member 230c. The engagement member 230c is configured to engage the annular ridges 224 formed on the outer surface 220c of the anchor cartridge 212, so as to prevent the anchor cartridge from inadvertently backing out of the bore 210. The engagement member 230c can have the shape of a tooth configured to engage an annular ridge 224, or any other shape as desired. The arm 230 also has a release tab 230d disposed proximate to the proximal end 230a. The release tab 230d is configured to cause the arm 230, and thus the engagement member 230c, to deflect away from the anchor cartridge 212 when a downward force is applied to the release tab 230d.

Figure 14:
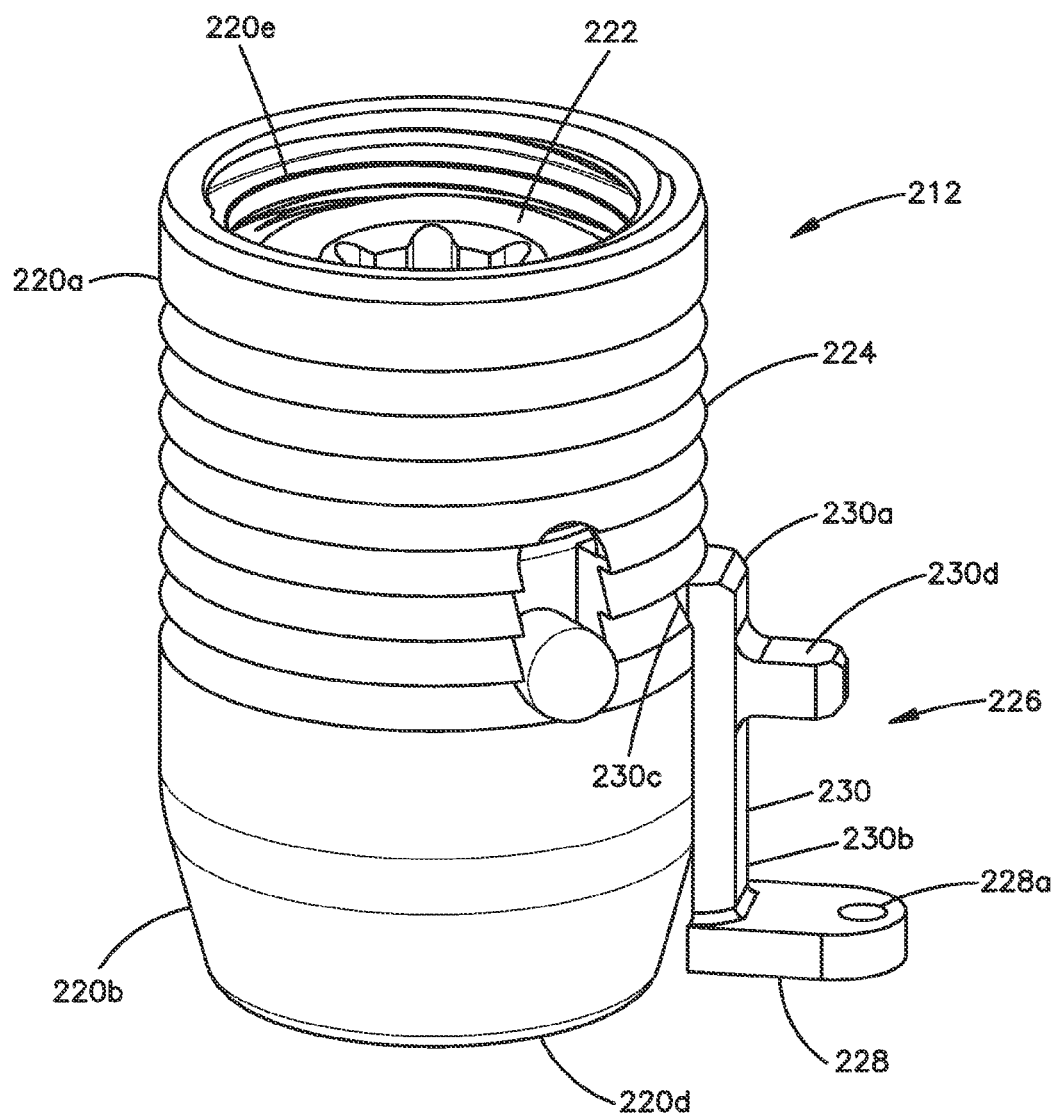
FIG. 14 is a perspective view of the anchor cartridge illustrated in FIG. 13 in an assembled configuration.
Figure 15A:
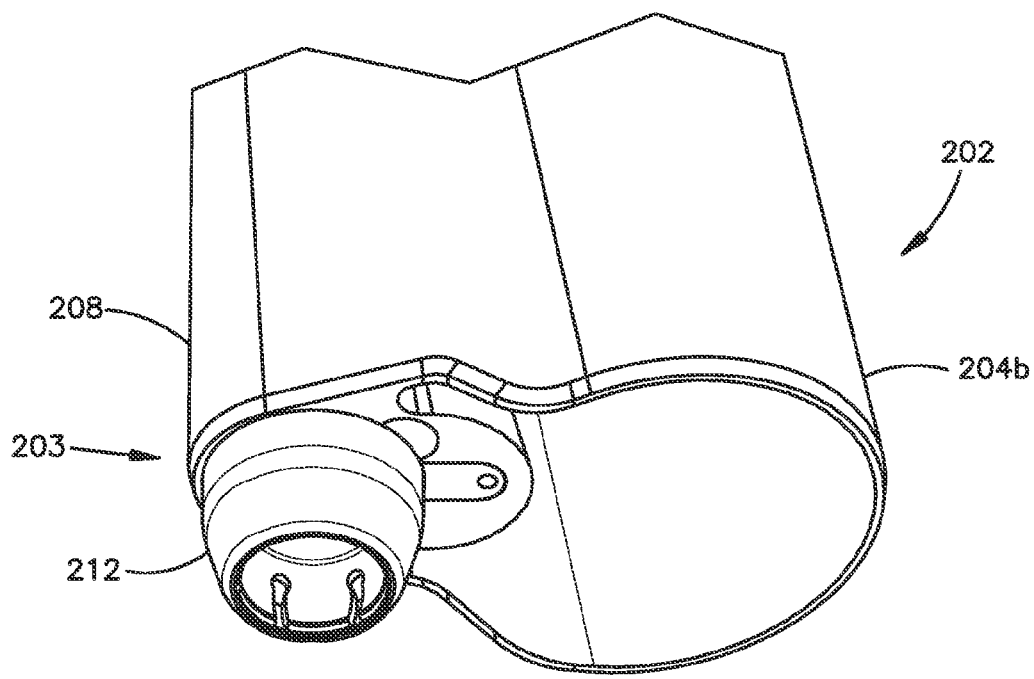
FIGS. 15A and 15B are perspective view of the distal end of the tube type patient-mounted retractor illustrated in FIG. 10 with the anchor cartridge disposed therein in extended and fully inserted configurations respectively.
Figure 15B:
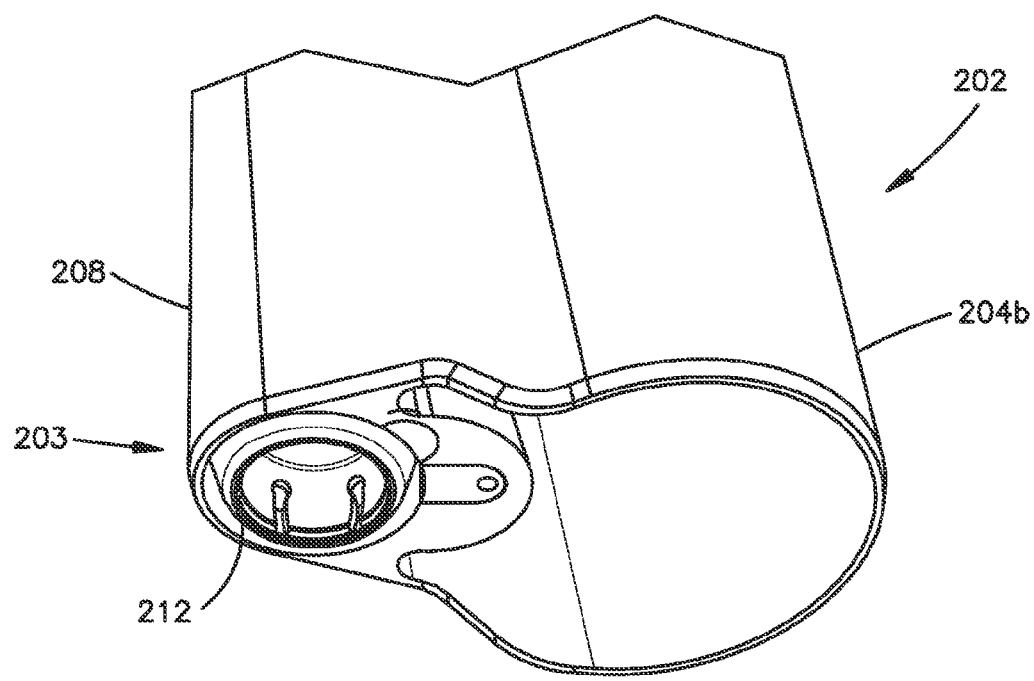

In accordance with the example embodiment illustrated in FIGS. 10-15B, as the anchor cartridge 212 is inserted into the bore 210 in the distal end 208b of the anchor receptacle 208, with the proximal end 220a inserted first, the outer surface 220c of the proximal end 220a of the anchor cartridge 212 interferes with the engagement member 230c on the arm 230 of the pawl 226, thereby causing the proximal end 230a of the arm 230 to deflect outwardly, away from the anchor cartridge 212. As the anchor cartridge 212 is further inserted, the engagement member 230c falls into the first of the annular ridges 224, and will snap back into its non-deflected state. At this point, the anchor cartridge 212 will be in an extended state, as depicted in FIG. 15A. The engagement member 230c will hug the annular ridge 224 that it engages, thereby preventing the anchor cartridge 212 from inadvertently backing out of the bore 210. As the anchor cartridge 212 is advanced further into the bore 210, the engagement member 230c rides up along each subsequent annular ridge 224, the proximal end 230a of the arm deflecting outwardly away from the anchor cartridge 212, then snapping back into its non-deflected state as is passes by the apex of each successive annular ridge 224. Eventually the anchor cartridge 212 becomes fully inserted into the bore 210, as illustrated in FIG. 15B. It should be noted that the annular ridges 224 and complimentary pawl 226 are merely example implementations that facilitate the axial translation of the anchor cartridge, and the scope of the instant disclosure should not be limited thereto.

In preferred embodiments, the tube type retractor 202 and the mounting post 115 are configured to allow the retractor 202 to be rotatable or polyaxially positionable about the mounting post 115 when the retractor 202 is connected to the mounting post 115. When the tube type retractor 202 is connected to the mounting post 115, for example bone anchor 116, and positioned as desired within the surgical site, the retractor body 204 can be fixed with respect to the mounting post 115 by engaging the locking assembly 500 disposed in the aperture 222 of the anchor cartridge 212 to a locked configuration. In the example embodiment the locking assembly 500 includes the locking components depicted in FIGS. 10-14, including a collet 232, an intermediate wedge 244, the locking cap 138, and a peg 256 that rotatably secures the collet 232 and the intermediate wedge 244. In alternative embodiments, the locking assembly 500 can include locking components similar to those described above with respect to the locking assembly 400 that is disposed within the aperture 108 of the anchor receptacle 106. In particular, the locking assembly 500 can include a collet (e.g., collets 128, 154, 156, or 232), a locking cap 138 usable with select ones of the collets, an intermediate wedge (e.g., intermediate wedges 144 or 244), and the peg 256.

The collet 232 includes an annular body 234 that defines a proximal end 234a, a distal end 234b opposite the proximal end, a concave inner surface 234c, and an opposing convex outer surface 234d. The annular body 234 can define the shape of a segment of a sphere, having a diameter or cross-sectional dimension that is greater at a location between the proximal and distal ends than at either of the proximal and distal ends 234a and 234b. The collet 232 has a pair of notches 236 formed in the proximal end 234a. The notches 236 are configured to engage complimentary tabs 252 formed on the lower surface 246b of the intermediary wedge 244.

The concave inner surface 234c may define a spherical shape that substantially matches the curved outer surface 122c of the head 120 of the bone anchor 116, such that the concave inner surface 234c engages the curved outer surface 122c when the head 120 of the bone anchor 116 is received in the collet 232. The inner surface of the socket 220d may be configured in the shape of a segment of a sphere with a spherical volume that is substantially the same as or slightly greater in magnitude than the spherical volume of the convex outside surface 234d of the collet 232. The annular body 234 further includes a plurality of circumferentially spaced retention fingers 240 formed within the distal end 234b of the annular body 234. The retention fingers 240 are configured such that circumferentially adjacent fingers are separated by a slot 242 that extends proximally upwards into the body 234 from the distal end 234b.

The retention fingers 240 are configured to retain the head 120 of the bone anchor 116. As the collet 232 is first placed over the head 120 of the bone anchor 116, the retention fingers 240 deflect, spreading outwardly from the center of the collet 232 along the curved outer surface 122c of the head 120. Once the tips of the fingers 240 move beyond the portion of the curved outer surface 122c with the largest diameter between the proximal and distal ends 122a and 122b, the fingers 240 "snap" back to their original shape, thus releasably retaining the head 120 of the bone anchor within the collet 232 via a snap fit. The spherical inner surface of the socket 220d is sufficiently sized to accommodate snapping the collet 232 into place over the head 120 of the bone anchor 116, and for removal of the bone anchor 116 from the collet 232, while the collet 232 and the bone anchor 116 are disposed within the anchor cartridge 212.

The locking assembly 500 can further include a locking cap 138 and an intermediate wedge 244 that retain the collet 232 in the aperture 222 of the anchor cartridge 212. The intermediate wedge 244 may be disposed within the aperture 222 of the anchor cartridge 212 at a location between the collet 232 and the locking cap 138. The intermediate wedge 244 includes a generally cylindrical shaped body 246 defining an upper surface 246a at the proximal end of the body 246 and an opposing lower surface 246b at the distal end of the body 246. The body 246 further includes a raised collar 248 extending upwardly from the center of the upper surface 246a at the proximal end of the body 246. The collar 248 is configured to be received within the longitudinal aperture 140d of the locking cap 138. A longitudinal aperture 250 may be formed through the raised collar 248 and the body 246, the diameter of the aperture 250 sufficiently large to allow a guide wire to pass through. The intermediate wedge 244 includes a pair of tabs 252 that extend downward in a distal direction from the lower surface 246b of the body 246. The tabs 252 are configured to engage the notches 236 of the collet 232. The intermediate wedge 244 can define a radial aperture 254 formed in the wedge body 246 at a location between the upper and lower surfaces 246a and 246b.

The locking assembly 500 further includes a peg 256 that can be inserted into the slot 220f formed in the anchor cartridge 212 and received in the radial aperture 254 when the collet 232 and the intermediate wedge 244 are disposed in the aperture 222 and engaged with each other, so as to prevent axial rotation of the collet 232 and the intermediate wedge 244 within the aperture 222. The peg 256 can be configured such that tip of the peg 256 protrudes from the slot 220f when the peg 256 is seated within the radial aperture 254, such that when the anchor cartridge 212 is inserted into the bore 210 of the anchor receptacle 208, the tip of the peg is slidably engaged within a longitudinal groove 257 defined in the bore 210 and extending upwardly in a proximal direction from the distal end 208b of the anchor receptacle 208. When the tip of the peg 256 is disposed within the longitudinal groove 257, axial rotation of the anchor cartridge 212, and thus the collet 232 and the intermediate wedge 244, with respect to the bore 210 is prevented. Additionally, the peg 256 can be configured to limit axial translation of the collet 232 and the intermediate wedge 244 within the anchor receptacle 212 when the peg is disposed in the slot 220f and received in the radial aperture 254, as illustrated in FIG. 14.

It should be noted that the locking assembly 400 described above with reference to the blade type patient-mounted retractor 102, in particular the collets 128, 154, and 156, and the intermediate wedge 144, may be disposed within the aperture 222 of the anchor cartridge 212, in lieu of the collet 232 and the intermediary wedge 244. Similarly, it should be noted that the locking assembly 500 described above with reference to the tube type patient-mounted retractor 202, in particular the collet 232 and the intermediate wedge 244, may be disposed within the aperture 108 of the anchor receptacle 106 in lieu of the collets 128, 154, and 156, and the intermediate wedge 144.

In an example method of using the tube type patient-mounted retractor 202, the mounting post 115, for example the bone anchor 116, is inserted into the target location 109 of a patient. A tube type retractor 202 may then be connected to the head 120 of the bone anchor 116. The anchor receptacle 208 can be disposed at the distal end 204b of the body 204. The anchor receptacle 208 may include the anchor cartridge 212 carried in the bore 210. The anchor cartridge 212 may retain the components of the locking assembly 500. To aide deployment of the tube type patient-mounted retractor 202, it may be desirable to first locate a desired insertion point for the bone anchor via the insertion of a guide wire. A cannulated version of the bone anchor 116 may then be inserted into the surgical site over the guide wire to guide the trajectory of the bone anchor as it is driven into place. The guide wire may also be passed through the anchor cartridge 212 and the locking components therein, and used to guide the alignment of the collet with the head of the bone anchor.

The retractor 202 may be connected to the bone anchor 116 by snapping the collet 232 that is disposed in the anchor cartridge 212 over the head 120 of the bone anchor 116. When the retractor body 204 is connected to the head 120 of the bone anchor 116, the retractor 202 is rotatably positionable about the head 120 of the bone anchor 116. The retractor 202 is also axially translatable on the anchor cartridge 212. The retractor 202 may be moved closer to the underlying anatomy at the surgical site, for instance the target location 109, by applying a downward force to the retractor body 204, causing the anchor cartridge 212 to advance within the bore 210. The anchor cartridge 212 may be backed out of the bore 210 by applying a downward force, for example by an instrument inserted into access channel 208d, on the release tab 230d, causing the arm 230 of the pawl 226, and thus the engagement member 230c, to deflect away from the anchor cartridge 212 and to disengage from the annular rings 224. The retractor 202 can then be backed out of the bore 210, or translated away from the target location 109 by lifting up on the retractor body 204. When positioning the retractor 202 within the surgical site at the target location 109, one or more dilators configured for use with the retractor 202 may be used to initially retract patient anatomy from the surgical site.

Figure 17:
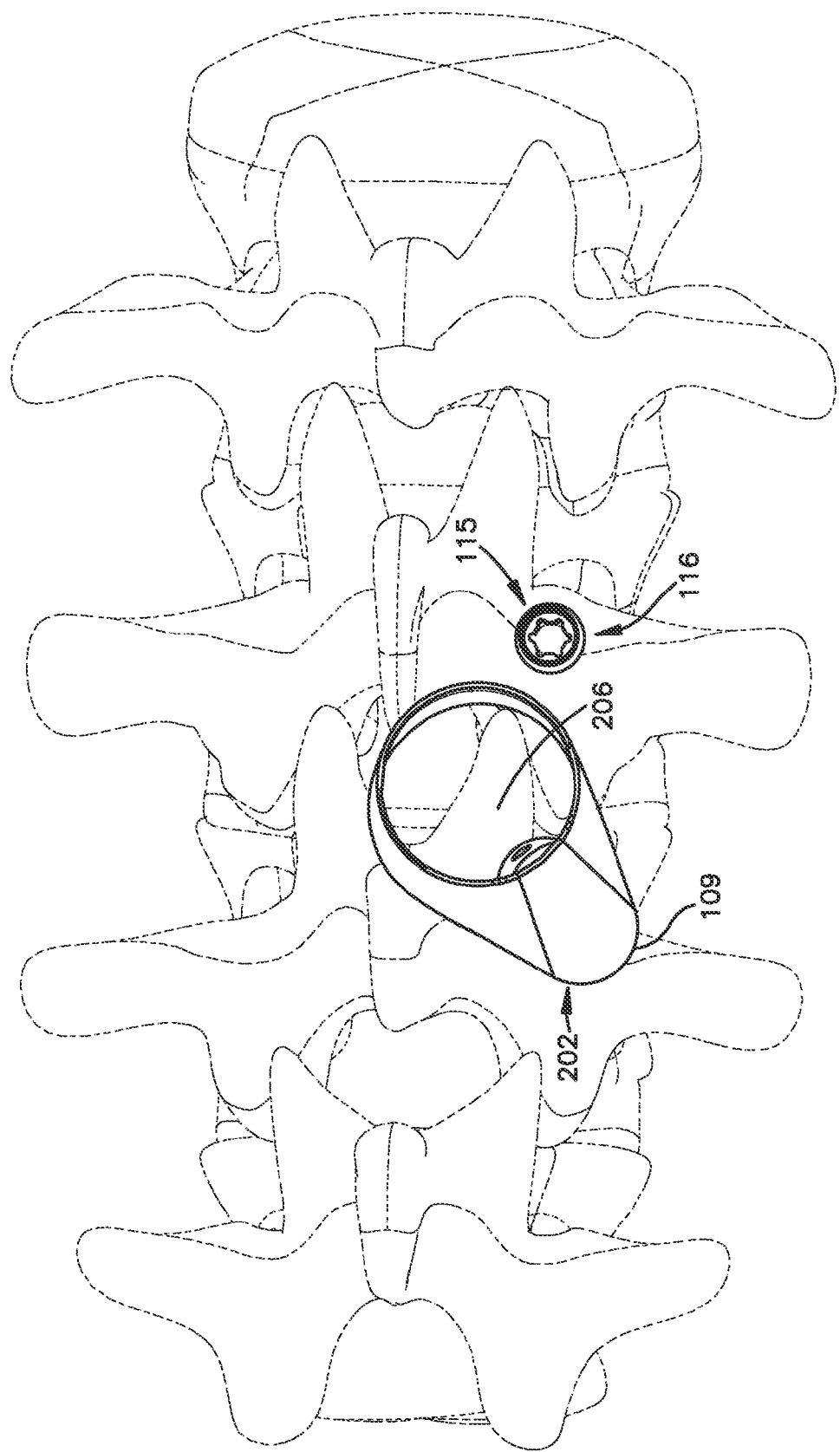
FIG. 17 is a perspective view of the tube type patient-mounted retractor assembly illustrated in FIG. 16.
Figure 18:
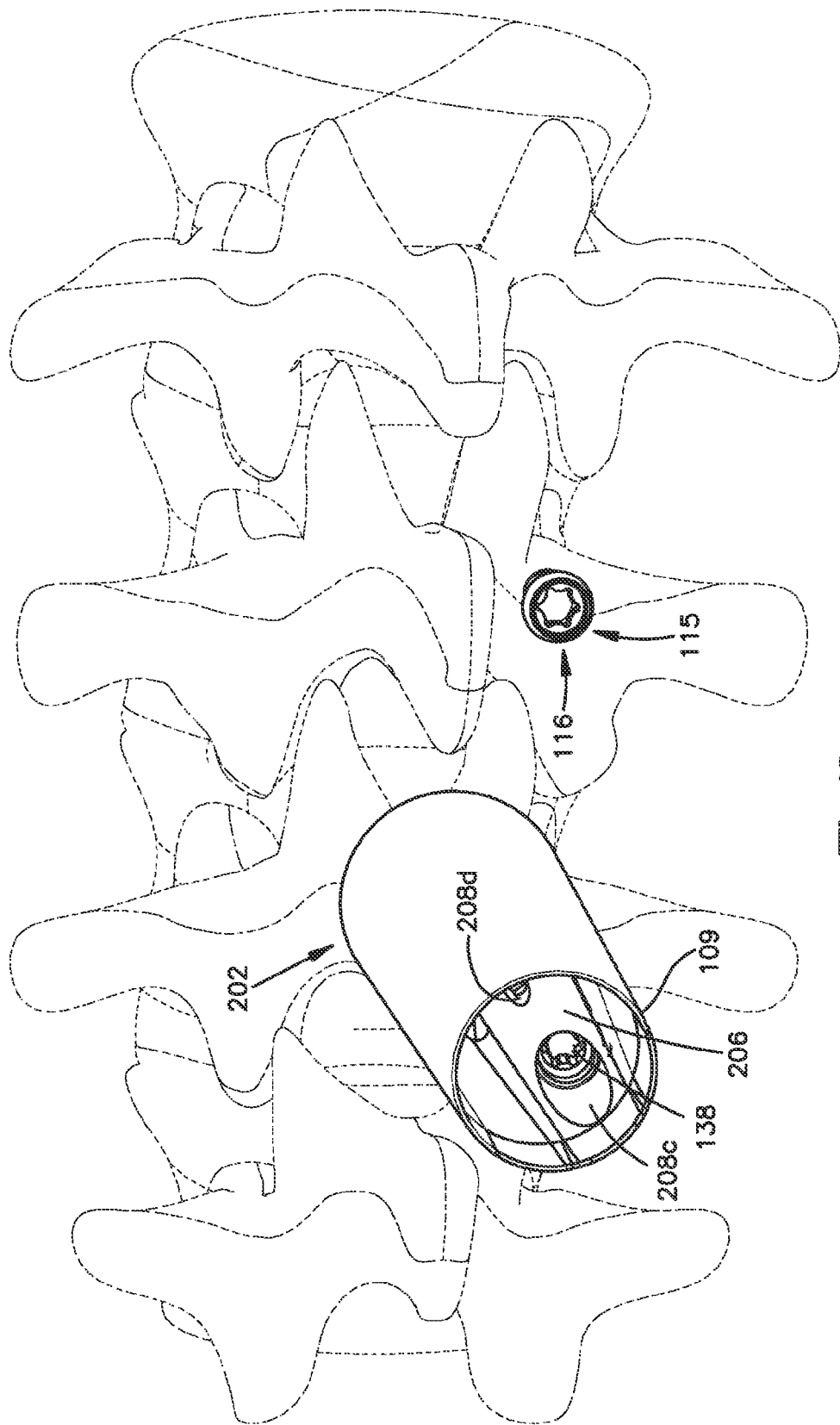
FIG. 18 is another perspective view of the tube type patient-mounted retractor assembly illustrated in FIG. 16.

Referring now to FIGS. 16-18 in particular, once the tube type retractor 202 has been positioned to provide the desired access portal into the surgical site, the retractor body 202 may be positionally fixed with respect to the bone anchor 116 by activating the locking assembly 500 to a locked configuration. In one example, a driving instrument may be inserted into the access channel 208c of the retractor 202, and a rotational driving force can be applied to the locking cap 138, thereby advancing the locking 138 cap in a distal, or downward, direction within the anchor cartridge 212, toward the collet 232. The advancing locking cap 138 transfers downward force to the intermediate wedge 244, causing the intermediate wedge 244 to be advanced in a downward direction within the anchor receptacle 212. As the intermediate wedge 244 advances downward, the tabs 252 of the intermediate wedge 244 engage the slots 236 of the collet 232, transferring downward force from the intermediate wedge 244 to the collet 232, thereby causing the retention fingers 240 to interfere with the inner surface of the socket 220d at the distal end 220b of the anchor cartridge 212, and to collapse around the head 120 of the bone anchor 116, thereby fixing the anchor receptacle, and thus the retractor body 204, in position with respect to the head 120 of the bone anchor 116 via a crush lock between the collet 232 and the bone anchor 116.

If a surgeon performing a procedure desires to reposition the tube type patient-mounted retractor 202 during a procedure, a rotational driving force of the opposite direction to that applied during activation of the locking assembly 500 may be applied to release the locking assembly 500 to an unlocked configuration, thereby allowing the retractor 202 to be polyaxially positionable with respect to the bone anchor 116. The retractor 202 can further be axially translated with respect to the anchor cartridge 212 by applying a downward force to the release tab 230d of the pawl 226. When the retractor 202 is repositioned as desired, the locking assembly 500 can be activated again to its locked configuration as described above to re-lock the retractor body 204 in position with respect to the head 120 of the bone anchor 116. The tube type patient-mounted retractor 202 can be removed from the surgical site by releasing the locking assembly 500 and applying an upward force to the retractor body 204, thereby causing the collet 232 to disengage from the head 120 of the bone anchor 116. The bone anchor 116 may then be removed from the surgical site, or may be re-used, for example as a bone anchoring element of a bottom-loading pedicle screw assembly. It should be noted that while the instant example method is discussed within reference to the tube type patient-mounted retractor 202, it is possible to use blade type patient-mounted retractors 102 in combination with tube type patient-mounted retractors 202 during a single procedure. For example, if a procedure calls for incisions into multiple target locations 107 and/or 109, one or more blade type retractors 102 may be disposed at the target location 107, while a tube type retractor 202 may be disposed at the target location 209.

It should be appreciated that a variety of kits, for example surgical kits assembled for particular procedures, can be provided that include one or more components of the patient mounted retractor assemblies 100, 200 and systems disclosed herein. The components of the kits may be configured the same or differently. For example, within a single kit, a variety of blade type patient-mounted retractors 102 may be provided that have different retractor body geometries, different materials of manufacture, different locking assembly components or none at all, may or may not include an anchor receptacle, may or may not have a bore within the anchor receptacle for receiving an anchor cartridge, may or may not have one or more flanges formed thereon, may or may not have tabs formed at the distal ends of the flanges, may or may not have one or more sections of flexible skirting affixed to the distal ends of the flanges, etc., depending, for example, on the type of procedure being performed by a surgeon, on the particular surgical site location within a patient, on the size and/or anatomy of a patient, and the like. Alternatively, a kit may be configured with a plurality of identical blade type patient-mounted retractors 102. Within another single kit, a variety of tube type patient-mounted retractors 202 may be provided that have different retractor body geometries and/or different bore geometries, different heights, different materials of manufacture, different locking assembly components or none at all, may or may not include an anchor receptacle, may or may not have a bore within the anchor receptacle for receiving an anchor cartridge, may or may not have tabs formed at the distal ends of the retractor bodies, may or may not have one or more sections of flexible skirting affixed to the distal ends of the retractor bodies, etc., depending, for example, on the type of procedure being performed by a surgeon, on the particular surgical site location within a patient, on the size and/or anatomy of a patient, and the like. Alternatively, a kit may be configured with a plurality of identical tube type patient-mounted retractors 102.

The kits may also be configured differently with respect to which components of the individual patient-mounted retractor assemblies 100, 200 are included in the kits. For example, a single kit may include one or more blade and tube type patient-mounted retractors of various configurations and/or geometries, various locking assembly components, mounting posts of various types, for example bone anchors of varying lengths with polyaxial heads, dilators, guide wires of various lengths and/or diameters, and the like. Example kits may also include driving instruments.

Although blade and tube type patient-mounted retractors have been described herein with reference to preferred embodiments or preferred methods, it should be understood that the words which have been used herein are words of description and illustration, rather than words of limitation. For example, it should be appreciated that the various structure, features, and methods described above with respect to the blade type patient-mounted retractors may be combined with or otherwise integrated with the various structure, features, and methods described above with respect to the tube type patient-mounted retractors, and that similarly the various structure, features, and methods described above with respect to the tube type patient-mounted retractors may be combined with or otherwise integrated with the various structure, features, and methods described above with respect to the blade type patient-mounted retractors. Furthermore, it should be noted that although the blade and tube type patient-mounted retractors have been described herein with reference to particular structure, methods, and/or embodiments, the scope of the instant disclosure is not intended to be limited to those particulars, but rather is meant to extend to all structures, methods, and/or uses of blade and/or tube type patient-mounted retractors. Those skilled in the relevant art, having the benefit of the teachings of this specification, may effect numerous modifications to the blade and/or tube type patient mounted retractors and their corresponding assemblies as described herein, and changes may be made without departing from the scope and spirit of the instant disclosure, for instance as recited in the appended claims.

What is claimed:

1. A retractor assembly comprising:
    a retractor body including a proximal end defined along a first axis and a distal end opposite the proximal end, the proximal end defining an inner surface that faces the first axis, and an outer surface opposed to the inner surface, wherein at least a portion of the retractor body is open so as to define a channel, the channel being elongate along the first axis, and the retractor body further defines at least one flange extending outwardly therefrom between the proximal and distal ends;
    an anchor receptacle disposed at the distal end of the retractor body, the anchor receptacle defined along a second axis that extends through the channel, the anchor receptacle having an anchor receptacle proximal end and an anchor receptacle distal end that is spaced from the anchor receptacle proximal end along the second axis, wherein the channel is open from the proximal end of the retractor body toward the anchor receptacle proximal end,
    wherein the second axis is offset with respect to the first axis such that 1) an entirety of the proximal end of the retractor body is offset from the second axis in a direction that is perpendicular to the second axis, and 2) the outer surface of the proximal end of the retractor body faces the second axis; and
    a locking assembly carried by the anchor receptacle, the locking assembly configured to attach to the retractor body and to a bone anchor that is configured to be driven into an underlying target location of a patient such that the bone anchor is connectable to the retractor body.

2. The retractor assembly of claim 1, wherein when the retractor body is connected to the bone anchor, the locking assembly is configured to lock or unlock rotation of the retractor body relative to the bone anchor.

3. The retractor assembly as recited in claim 2, wherein when the locking assembly is locked, the retractor body is configured to be positionally fixed relative to the bone anchor, and when the locking assembly is unlocked, the retractor body is not positionally fixed relative to the bone anchor.

4. The retractor assembly as recited in claim 3, wherein the locking assembly comprises:
    a collet having a proximal end, a distal end opposite the proximal end, and an interior volume defined within the distal end of the collet, the interior volume configured to capture and retain a head of the bone anchor; and
    a locking cap having a threaded outer surface configured to engage complimentary threads formed within the anchor receptacle,
    wherein application of a rotational force to the locking cap advances the locking cap within the anchor receptacle, thereby causing the collet to create an interference force between the head of the bone anchor and the anchor receptacle.

5. The retractor assembly as recited in claim 4, wherein the collet has a plurality of slots formed in the distal end of the collet, the slots defining a plurality of deflectable fingers.

6. The retractor assembly as recited in claim 4, wherein the proximal end of the collet has an upper surface with an engagement structure formed thereon, the engagement structure configured to engage a lower surface of the locking cap.

7. The retractor assembly as recited in claim 4, further comprising a wedge disposed between the collet and the locking cap, the wedge configured to distribute force from the locking cap to the collet when the locking cap is advanced within the anchor receptacle.

8. The retractor assembly as recited in claim 1, further comprising the bone anchor.

9. The retractor assembly as recited in claim 8, wherein the bone anchor has a polyaxial head.

10. The retractor assembly as recited in claim 9, wherein the retractor body is rotatably positionable about the polyaxial head of the bone anchor when the polyaxial head of the bone anchor is received in the anchor receptacle.

11. The retractor assembly as recited in claim 1, wherein the retractor body defines an aperture formed therethrough, the aperture extending along an aperture axis that is aligned with the second axis, the aperture configured to receive a driving instrument.

12. The retractor assembly as recited in claim 1, wherein the retractor body includes a first lateral edge and a second lateral edge, and the first and second lateral edges extend from the proximal end of the retractor body toward the distal end of the retractor body, wherein retractor body, the first lateral edge and the second lateral edge define the channel, and the retractor body is open from the proximal end of the retractor body to the anchor receptacle proximal end.

13. The retractor assembly as recited in claim 12, wherein the anchor receptacle extends around an entirety of the second axis.

14. The retractor assembly as recited in claim 1, the retractor body further defining an intermediate portion that extends between the proximal and distal ends along a third axis that is offset with respect to the first and second axes, wherein the channel surrounds the first, second, and third axes.

15. The retractor assembly as recited in claim 14, wherein the intermediate portion is open.

16. The retractor assembly as recited in claim 15, wherein the intermediate portion defines at least a portion of the channel.

17. The retractor assembly as recited in claim 16, wherein the intermediate portion of the retractor body has an aperture formed therethrough, the aperture configured to receive a driving instrument.

18. The retractor assembly as recited in claim 14, wherein a cross sectional dimension of the intermediate portion varies in magnitude between the proximal and distal ends.

19. The retractor assembly as recited in claim 18, wherein the cross sectional dimension of the intermediate portion increases in magnitude between the proximal and distal ends.

20. The retractor assembly as recited in claim 18, wherein the cross sectional dimension of the intermediate portion decreases in magnitude between the proximal and distal ends.

21. The retractor assembly as recited in claim 14, wherein the intermediate portion is defined along the third axis, and the intermediate portion defines an offset region between the proximal and distal ends.

22. The retractor assembly as recited in claim 1, wherein the retractor body defines a lateral edge that extends between the proximal and distal ends of the retractor body, and the at least one flange extends along the lateral edge of the retractor body adjacent the channel.

23. The retractor assembly as recited in claim 1, wherein the at least one flange extends along a chord defined between two points on a circumference of the retractor body.

24. The retractor assembly as recited in claim 1, wherein the at least one flange has a tab formed at a distal end of the flange.

25. The retractor assembly as recited in claim 24, wherein the tab is configured to flexibly conform to bony geometry within a surgical site.

26. The retractor assembly as recited in claim 25, wherein the tab comprises a flexible skirt.

27. The retractor assembly as recited in claim 1, wherein the at least one flange is configured to form at least a portion of an access portal within a surgical site.

28. The retractor assembly as recited in claim 1, wherein the retractor body defines an accessory attachment point configured to releasably engage an optional accessory.

29. The retractor assembly as recited in claim 1, wherein the first and second axes are substantially parallel with respect to each other.

30. The retractor assembly of claim 1, wherein the locking assembly comprises a collet having a proximal end, a distal end opposite the proximal end of the collet, and an interior volume defined within the distal end of the collet, the interior volume configured to capture and retain a head of the bone anchor by snapping the collet over the head of the bone anchor.

31. The retractor assembly as recited in claim 1, wherein the channel is open from the proximal end to the proximal end of the anchor receptacle.

32. The retractor assembly of claim 1, wherein the anchor receptacle defines a bore that extends from the anchor receptacle proximal end to the anchor receptacle distal end, and at least a portion of the locking assembly is disposed in the bore.

33. The retractor assembly of claim 1, wherein the channel partially surrounds the first axis and the second axis such that the retractor body faces the first and second axes.

34. A retractor assembly comprising:
a cannulated retractor body having a proximal end, a distal end spaced apart from the proximal end along a first axis, and a bore that extends from the proximal end to the distal end along the first axis, the proximal end being centrally disposed along the first axis;
a bone anchor including a distal end configured to be removably mounted to a vertebral body of a patient, the bone anchor having a head spaced from the distal end of the bone anchor;
an anchor receptacle that is configured to receive the bone anchor and extends from the cannulated retractor body along a second axis that is angularly offset with respect to the first axis, such that a distance between the first and second axes at the proximal end of the cannulated retractor body is less than a distance between the first and second axes at the distal end of the cannulated retractor body, the anchor receptacle having a first end disposed along the cannulated retractor body and a second end spaced apart from the first end along the second axis, wherein an entirety of the second end of the anchor receptacle is spaced from the distal end of the cannulated retractor body along a direction that is transverse to the first axis; and
a locking assembly configured to attach to the cannulated retractor body and within the anchor receptacle, the locking assembly further configured to attach to the head of the bone anchor such that when the cannulated retractor body is attached to the head of the bone anchor the second axis extends through the head of the bone anchor and the cannulated retractor body is selectively 1) polyaxially positionable with respect to the bone anchor or, 2) locked in a fixed position with respect to the bone anchor.

35. The retractor assembly as recited in claim 34, wherein the locking assembly is disposed within an anchor cartridge, the anchor cartridge configured to be received within the anchor receptacle.

36. The retractor assembly as recited in claim 35, wherein the anchor cartridge is configured for axially adjustable engagement within the anchor receptacle.

37. The retractor assembly as recited in claim 36, wherein the anchor cartridge has an outer surface with a plurality of annular ridges formed thereon, the annular ridges configured to releasably engage with a complimentary engagement member of the anchor receptacle.

38. The retractor assembly of claim 34, wherein the bore of the cannulated retractor body extends from a proximal opening disposed at the proximal end of the cannulated retractor body to a distal opening disposed at the distal end of the cannulated retractor body, wherein the anchor receptacle defines a bore that extends along the second axis.

39. The retractor assembly as recited in claim 38, wherein the anchor receptacle defines a channel having a first end that is open to the bore of the cannulated retractor body at a location between the proximal and distal openings and a second end that is adjacent to the anchor receptacle.

40. The retractor assembly of claim 34, wherein the locking assembly comprises:
   a collet having a proximal end, a distal end opposite the proximal end, and an interior volume defined within the distal end of the collet, the interior volume configured to capture and retain the head of the bone anchor; and
   a locking cap having a threaded outer surface configured to engage complimentary threads formed within the anchor receptacle.

41. The retractor assembly of claim 34, wherein the anchor receptacle defines a bore that extends along the second axis, and the second axis intersects the first axis.

42. A surgical kit comprising:
   a first retractor body extending between a first proximal end and a first distal end opposed to the first proximal end, the first proximal end defined along a first axis, the first distal end of the first retractor body defining a first mounting member, the first mounting member being defined along a second axis that is offset with respect to the first axis such that the first mounting member is spaced apart from the first axis along a direction that is transverse to the first axis, the first mounting member extending around an entirety of the second axis, the first mounting member configured to rotatably attach to a first bone anchor that is configured to be disposed in a patient, wherein the first retractor body is rotatable about the first bone anchor when the mounting member is attached to the first bone anchor, and the retractor body defines a channel that extends from the first proximal end to the first distal end, such that the first and second axes extend through the channel; and
   a second retractor body extending between a second proximal end defined along a third axis and an opposed second distal end defined along a fourth axis that is offset with respect to the third axis, the second retractor body having a second mounting member defined along the fourth axis, the second mounting member configured to rotatably attach to a second bone anchor disposed in the patient such that the second retractor body is rotatable about the fourth axis.

43. The surgical kit as recited in claim 42, further comprising a plurality of bone anchors, wherein the first and second mounting members comprise first and second anchor receptacles, respectively, and the first and second anchor receptacles are each configured to connect to a respective one of the plurality of bone anchors.

44. The surgical kit as recited in claim 43, further comprising a plurality of locking components configured to be received within the first and second anchor receptacles.

45. The surgical kit as recited in claim 42, wherein the first and second retractor bodies define identical body geometries.

46. The surgical kit as recited in claim 42, wherein the first and second retractor bodies define different body geometries.

47. The surgical kit of claim 42, wherein an entirety of the first mounting member is spaced apart from the first axis along the direction that is transverse to the first axis.

\* \* \* \* \*